US008486387B2

(12) United States Patent
Michal et al.

(10) Patent No.: US 8,486,387 B2
(45) Date of Patent: Jul. 16, 2013

(54) MODIFIED TWO-COMPONENT GELATION SYSTEMS, METHODS OF USE AND METHODS OF MANUFACTURE

(75) Inventors: Eugene Michal, San Francisco, CA (US); Olof Mikael Trollsas, San Jose, CA (US); Shubhayu Basu, Mountain View, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 513 days.

(21) Appl. No.: 12/756,119

(22) Filed: Apr. 7, 2010

(65) Prior Publication Data

US 2010/0196314 A1    Aug. 5, 2010

Related U.S. Application Data

(62) Division of application No. 11/496,824, filed on Jul. 31, 2006, now Pat. No. 7,732,190.

(51) Int. Cl.
| | |
|---|---|
| *A61K 31/00* | (2006.01) |
| *A61K 9/00* | (2006.01) |
| *A61M 5/19* | (2006.01) |
| *A61K 38/18* | (2006.01) |
| *A61M 5/00* | (2006.01) |
| *A61M 31/00* | (2006.01) |
| *A61P 9/00* | (2006.01) |

(52) U.S. Cl.
USPC ........ 424/93.7; 424/85.1; 424/85.2; 424/450; 514/7.6; 514/8.2; 514/16.4; 435/810; 604/191; 604/158

(58) Field of Classification Search
None
See application file for complete search history.

(56) References Cited

U.S. PATENT DOCUMENTS

| 2,512,569 A | 6/1950 | Saffir |
| 3,144,868 A | 8/1964 | Jascalevich |

(Continued)

FOREIGN PATENT DOCUMENTS

| EP | 0331584 | 9/1989 |
| EP | 0861632 | 9/1998 |

(Continued)

OTHER PUBLICATIONS

Xiaojin Hao, Eduardo A. Silva, Agneta Månsson-Broberg, Karl-Henrik Grinnemo, Anwar J. Siddiqui, Göran Dellgren, Eva Wärdell, Lars Åke Brodin, David J. Mooney, Christer Sylven "Angiogenic"Effects of Sequential Release of VEGF-A165 and PDGF-BB with Alginate Hydrogels After Myocardial Infarction Cardiovascular Research, Apr. 6, 2007,75(1),pp. 178-185.*

(Continued)

*Primary Examiner* — Chris R Tate
*Assistant Examiner* — Aaron J Kosar
(74) *Attorney, Agent, or Firm* — Randy Shen; Blakely Sokoloff Taylor & Zafman LLP

(57) ABSTRACT

Compositions, methods of manufacture and methods of treatment for post-myocardial infarction are herein disclosed. In some embodiments, the composition includes at least two components. In one embodiment, a first component can include a first functionalized polymer and a substance having at least one cell adhesion site combined in a first buffer at a pH of approximately 6.5. A second component can include a second buffer in a pH of between about 7.5 and 9.0. A second functionalized polymer can be included in the first or second component. In some embodiments, the composition can include at least one cell type and/or at least one growth factor. In some embodiments, the composition(s) of the present invention can be delivered by a dual bore injection device to a treatment area, such as a post-myocardial infarct region.

14 Claims, 7 Drawing Sheets

U.S. PATENT DOCUMENTS

| | | |
|---|---|---|
| 3,584,624 A | 6/1971 | de Ciutiis |
| 3,780,733 A | 12/1973 | Martinez-Manzor |
| 3,804,097 A | 4/1974 | Rudie |
| 3,890,976 A | 6/1975 | Bazell et al. |
| 4,141,973 A | 2/1979 | Balazs |
| 4,617,186 A | 10/1986 | Schafer et al. |
| 4,794,931 A | 1/1989 | Yock |
| 4,818,291 A | 4/1989 | Iwatsuki et al. |
| 4,842,590 A | 6/1989 | Tanabe et al. |
| 5,000,185 A | 3/1991 | Yock |
| 5,024,234 A | 6/1991 | Leary et al. |
| 5,026,350 A | 6/1991 | Tanaka et al. |
| 5,049,130 A | 9/1991 | Powell |
| 5,092,848 A | 3/1992 | DeCiutiis |
| 5,100,185 A | 3/1992 | Menke et al. |
| 5,109,859 A | 5/1992 | Jenkins |
| 5,116,317 A | 5/1992 | Carson et al. |
| 5,128,326 A | 7/1992 | Balazs et al. |
| 5,171,217 A | 12/1992 | March et al. |
| 5,202,745 A | 4/1993 | Sorin et al. |
| 5,203,338 A | 4/1993 | Jang |
| 5,242,427 A | 9/1993 | Bilweis |
| 5,270,300 A | 12/1993 | Hunziker |
| 5,291,267 A | 3/1994 | Sorin et al. |
| 5,306,250 A | 4/1994 | March et al. |
| 5,321,501 A | 6/1994 | Swanson et al. |
| 5,328,955 A | 7/1994 | Rhee et al. |
| 5,336,252 A | 8/1994 | Cohen |
| 5,354,279 A | 10/1994 | Hofling |
| 5,365,325 A | 11/1994 | Kumasaka et al. |
| 5,372,138 A | 12/1994 | Crowley et al. |
| 5,380,292 A | 1/1995 | Wilson |
| 5,419,777 A | 5/1995 | Hofling et al. |
| 5,437,632 A | 8/1995 | Engelson |
| 5,455,039 A | 10/1995 | Edelman et al. |
| 5,459,570 A | 10/1995 | Swanson et al. |
| 5,464,395 A | 11/1995 | Faxon et al. |
| 5,465,147 A | 11/1995 | Swanson |
| 5,485,486 A | 1/1996 | Gilhousen et al. |
| 5,499,630 A | 3/1996 | Hiki et al. |
| 5,516,532 A | 5/1996 | Atala et al. |
| 5,540,912 A | 7/1996 | Roorda et al. |
| 5,546,948 A | 8/1996 | Hamm et al. |
| 5,554,389 A | 9/1996 | Badylak et al. |
| 5,575,815 A | 11/1996 | Slepian et al. |
| 5,580,714 A | 12/1996 | Polovina |
| 5,580,856 A | 12/1996 | Prestrelski et al. |
| 5,588,432 A | 12/1996 | Crowley |
| 5,621,610 A | 4/1997 | Moore et al. |
| 5,631,011 A | 5/1997 | Wadstrom |
| 5,642,234 A | 6/1997 | Altman et al. |
| 5,655,548 A | 8/1997 | Nelson et al. |
| 5,667,778 A | 9/1997 | Atala |
| 5,669,883 A | 9/1997 | Scarfone et al. |
| 5,672,153 A | 9/1997 | Lax et al. |
| 5,676,151 A | 10/1997 | Yock |
| 5,693,029 A | 12/1997 | Leonhardt |
| 5,722,403 A | 3/1998 | McGee et al. |
| 5,725,551 A | 3/1998 | Myers et al. |
| 5,730,732 A | 3/1998 | Sardelis et al. |
| 5,740,808 A | 4/1998 | Panescu et al. |
| 5,749,915 A | 5/1998 | Slepian |
| 5,785,689 A | 7/1998 | De Toledo et al. |
| 5,795,331 A | 8/1998 | Cragg et al. |
| 5,810,885 A | 9/1998 | Zinger |
| 5,811,533 A | 9/1998 | Gold et al. |
| 5,827,313 A | 10/1998 | Ream |
| 5,843,156 A | 12/1998 | Slepian et al. |
| 5,874,500 A | 2/1999 | Rhee et al. |
| 5,879,713 A | 3/1999 | Roth et al. |
| 5,900,433 A | 5/1999 | Igo et al. |
| 5,906,934 A | 5/1999 | Grande et al. |
| 5,919,449 A | 7/1999 | Dinsmore |
| 5,935,160 A | 8/1999 | Auricchio et al. |
| 5,939,323 A | 8/1999 | Valentini et al. |
| 5,941,868 A | 8/1999 | Kaplan et al. |
| 5,957,941 A | 9/1999 | Ream |
| 5,968,064 A | 10/1999 | Selmon |
| 5,979,449 A | 11/1999 | Steer |
| 5,980,887 A | 11/1999 | Isner et al. |
| 5,981,568 A | 11/1999 | Kunz et al. |
| 5,984,908 A | 11/1999 | Davis et al. |
| 5,997,536 A | 12/1999 | Osswald et al. |
| 6,022,540 A | 2/2000 | Bruder et al. |
| 6,045,565 A | 4/2000 | Ellis et al. |
| 6,050,949 A | 4/2000 | White et al. |
| 6,051,071 A | 4/2000 | Charvet et al. |
| 6,051,648 A | 4/2000 | Rhee et al. |
| 6,056,744 A | 5/2000 | Edwards |
| 6,058,329 A | 5/2000 | Salo et al. |
| 6,060,053 A | 5/2000 | Atala |
| 6,071,305 A | 6/2000 | Brown et al. |
| 6,086,582 A | 7/2000 | Altman et al. |
| 6,093,177 A | 7/2000 | Javier, Jr. et al. |
| 6,099,563 A | 8/2000 | Zhong |
| 6,099,864 A | 8/2000 | Morrison et al. |
| 6,102,887 A | 8/2000 | Altman |
| 6,102,904 A | 8/2000 | Vigil et al. |
| 6,102,926 A | 8/2000 | Tartaglia et al. |
| 6,120,520 A | 9/2000 | Saadat et al. |
| 6,120,904 A | 9/2000 | Hostettler et al. |
| 6,127,448 A | 10/2000 | Domb |
| 6,133,231 A | 10/2000 | Ferrara et al. |
| 6,134,003 A | 10/2000 | Tearney et al. |
| 6,146,373 A | 11/2000 | Cragg et al. |
| 6,151,525 A | 11/2000 | Soykan |
| 6,152,141 A | 11/2000 | Stevens et al. |
| 6,153,428 A | 11/2000 | Gustafsson et al. |
| 6,159,443 A | 12/2000 | Hallahan et al. |
| 6,162,202 A | 12/2000 | Sicurelli et al. |
| 6,175,669 B1 | 1/2001 | Colston et al. |
| 6,177,407 B1 | 1/2001 | Rodgers et al. |
| 6,179,809 B1 | 1/2001 | Khairkhahan et al. |
| 6,183,432 B1 | 2/2001 | Milo |
| 6,183,444 B1 | 2/2001 | Glines et al. |
| 6,187,330 B1 | 2/2001 | Wang et al. |
| 6,190,353 B1 | 2/2001 | Makower et al. |
| 6,191,144 B1 | 2/2001 | Isner |
| 6,192,271 B1 | 2/2001 | Hayman |
| 6,193,763 B1 | 2/2001 | Mackin |
| 6,197,324 B1 | 3/2001 | Crittenden |
| 6,201,608 B1 | 3/2001 | Mandella et al. |
| 6,206,893 B1 | 3/2001 | Klein et al. |
| 6,206,914 B1 | 3/2001 | Soykan et al. |
| 6,207,180 B1 | 3/2001 | Ottoboni et al. |
| 6,210,392 B1 | 4/2001 | Vigil et al. |
| 6,217,527 B1 | 4/2001 | Selmon et al. |
| 6,217,554 B1 | 4/2001 | Green |
| 6,221,049 B1 | 4/2001 | Selmon et al. |
| 6,231,546 B1 | 5/2001 | Milo et al. |
| 6,235,000 B1 | 5/2001 | Milo et al. |
| 6,241,710 B1 | 6/2001 | Van Tassel et al. |
| 6,251,104 B1 | 6/2001 | Kesten et al. |
| 6,283,947 B1 | 9/2001 | Mirzaee |
| 6,287,285 B1 | 9/2001 | Michal et al. |
| 6,290,729 B1 | 9/2001 | Slepian et al. |
| 6,296,602 B1 | 10/2001 | Headley |
| 6,299,604 B1 | 10/2001 | Ragheb et al. |
| 6,309,370 B1 | 10/2001 | Haim et al. |
| 6,312,725 B1 | 11/2001 | Wallace et al. |
| 6,315,994 B2 | 11/2001 | Usala et al. |
| 6,323,278 B2 | 11/2001 | Rhee et al. |
| RE37,463 E | 12/2001 | Altman |
| 6,328,229 B1 | 12/2001 | Duronio et al. |
| 6,331,309 B1 | 12/2001 | Jennings, Jr. et al. |
| 6,333,194 B1 | 12/2001 | Levy et al. |
| 6,334,872 B1 | 1/2002 | Termin et al. |
| 6,338,717 B1 | 1/2002 | Ouchi |
| 6,346,098 B1 | 2/2002 | Yock et al. |
| 6,346,099 B1 | 2/2002 | Altman |
| 6,346,515 B1 | 2/2002 | Pitaru et al. |
| 6,358,247 B1 | 3/2002 | Altman et al. |
| 6,358,258 B1 | 3/2002 | Arcia et al. |
| 6,360,129 B1 | 3/2002 | Ley et al. |
| 6,368,285 B1 | 4/2002 | Osadchy et al. |
| 6,371,935 B1 | 4/2002 | Macoviak et al. |
| 6,371,992 B1 | 4/2002 | Tanagho et al. |

| | | |
|---|---|---|
| 6,379,379 B1 | 4/2002 | Wang |
| 6,385,476 B1 | 5/2002 | Osadchy et al. |
| 6,391,052 B2 | 5/2002 | Buirge et al. |
| 6,395,023 B1 | 5/2002 | Summers |
| 6,409,716 B1 | 6/2002 | Sahatjian et al. |
| 6,416,510 B1 | 7/2002 | Altman et al. |
| 6,425,887 B1 | 7/2002 | McGuckin et al. |
| 6,432,119 B1 | 8/2002 | Saadat |
| 6,436,135 B1 | 8/2002 | Goldfarb |
| 6,440,947 B1 | 8/2002 | Barron et al. |
| 6,443,941 B1 | 9/2002 | Slepian et al. |
| 6,443,949 B2 | 9/2002 | Altman |
| 6,447,504 B1 | 9/2002 | Ben-Haim et al. |
| 6,458,095 B1 | 10/2002 | Wirt et al. |
| 6,458,098 B1 | 10/2002 | Kanesaka |
| 6,464,862 B2 | 10/2002 | Bennett |
| 6,465,001 B1 | 10/2002 | Hubbell et al. |
| 6,478,775 B1 | 11/2002 | Galt et al. |
| 6,478,776 B1 | 11/2002 | Rosenman et al. |
| 6,482,231 B1 | 11/2002 | Abatangelo et al. |
| 6,485,481 B1 | 11/2002 | Pfeiffer |
| 6,494,862 B1 | 12/2002 | Ray et al. |
| 6,514,217 B1 | 2/2003 | Selmon et al. |
| 6,544,230 B1 | 4/2003 | Flaherty et al. |
| 6,548,081 B2 | 4/2003 | Sadozai et al. |
| 6,554,801 B1 | 4/2003 | Steward et al. |
| 6,599,267 B1 | 7/2003 | Ray et al. |
| 6,602,241 B2 | 8/2003 | Makower et al. |
| 6,616,869 B2 | 9/2003 | Mathiowitz et al. |
| 6,624,245 B2 | 9/2003 | Wallace et al. |
| 6,628,988 B2 | 9/2003 | Kramer et al. |
| 6,629,947 B1 | 10/2003 | Sahatjian et al. |
| 6,632,457 B1 | 10/2003 | Sawhney |
| 6,635,267 B1 | 10/2003 | Miyoshi et al. |
| 6,660,034 B1 | 12/2003 | Mandrusov et al. |
| 6,682,730 B2 | 1/2004 | Mickel et al. |
| 6,689,608 B1 | 2/2004 | Mikos et al. |
| 6,692,466 B1 | 2/2004 | Chow et al. |
| 6,702,744 B2 | 3/2004 | Mandrusov et al. |
| 6,706,034 B1 | 3/2004 | Bhat |
| 6,726,677 B1 | 4/2004 | Flaherty et al. |
| 6,737,072 B1 | 5/2004 | Angele et al. |
| 6,748,258 B1 | 6/2004 | Mueller et al. |
| 6,749,617 B1 | 6/2004 | Palasis et al. |
| 6,759,431 B2 | 7/2004 | Hunter et al. |
| 6,761,887 B1 | 7/2004 | Kavalkovich et al. |
| 6,777,000 B2 | 8/2004 | Ni et al. |
| 6,777,231 B1 | 8/2004 | Katz et al. |
| 6,790,455 B2 | 9/2004 | Chu et al. |
| 6,824,791 B2 | 11/2004 | Mathiowitz et al. |
| 6,858,229 B1 | 2/2005 | Hubbell et al. |
| 6,916,488 B1 | 7/2005 | Meier et al. |
| 6,916,648 B2 | 7/2005 | Goddard et al. |
| 6,926,692 B2 | 8/2005 | Katoh et al. |
| 6,992,172 B1 | 1/2006 | Chang et al. |
| 7,008,411 B1 | 3/2006 | Mandrusov et al. |
| 7,035,092 B2 | 4/2006 | Hillman et al. |
| 7,112,587 B2 | 9/2006 | Timmer et al. |
| 7,129,210 B2 | 10/2006 | Lowinger et al. |
| 7,169,127 B2 | 1/2007 | Epstein et al. |
| 7,270,654 B2 | 9/2007 | Griego et al. |
| 7,273,469 B1 | 9/2007 | Chan et al. |
| 7,361,360 B2 | 4/2008 | Kitabwalla et al. |
| 7,374,774 B2 | 5/2008 | Bowlin et al. |
| 7,393,339 B2 | 7/2008 | Zawacki et al. |
| 7,438,692 B2 | 10/2008 | Tsonton et al. |
| 7,615,373 B2 | 11/2009 | Simpson et al. |
| 7,732,190 B2 | 6/2010 | Michal et al. |
| 7,815,590 B2 | 10/2010 | Cooper |
| 8,187,621 B2 | 5/2012 | Michal |
| 8,192,760 B2 | 6/2012 | Hossainy et al. |
| 2001/0023349 A1 | 9/2001 | Van Tassel et al. |
| 2001/0055615 A1 | 12/2001 | Wallace et al. |
| 2002/0013408 A1 | 1/2002 | Rhee et al. |
| 2002/0042473 A1 | 4/2002 | Trollsas et al. |
| 2002/0072706 A1 | 6/2002 | Hiblar et al. |
| 2002/0076441 A1 | 6/2002 | Shih et al. |
| 2002/0090725 A1 | 7/2002 | Simpson et al. |
| 2002/0102272 A1 | 8/2002 | Rosenthal et al. |
| 2002/0124855 A1 | 9/2002 | Chachques |
| 2002/0131974 A1 | 9/2002 | Segal |
| 2002/0142458 A1 | 10/2002 | Williams et al. |
| 2002/0146557 A1 | 10/2002 | Claude et al. |
| 2002/0151867 A1 | 10/2002 | McGuckin et al. |
| 2002/0169420 A1 | 11/2002 | Galt et al. |
| 2002/0188170 A1 | 12/2002 | Santamore et al. |
| 2003/0023202 A1 | 1/2003 | Nielson |
| 2003/0040712 A1 | 2/2003 | Ray et al. |
| 2003/0050597 A1 | 3/2003 | Dodge et al. |
| 2003/0078671 A1 | 4/2003 | Lesniak et al. |
| 2003/0105493 A1 | 6/2003 | Salo |
| 2003/0175410 A1 | 9/2003 | Campbell et al. |
| 2004/0002650 A1 | 1/2004 | Mandrusov et al. |
| 2004/0181206 A1 | 9/2004 | Chiu et al. |
| 2004/0185084 A1 | 9/2004 | Rhee et al. |
| 2004/0208845 A1 | 10/2004 | Michal et al. |
| 2004/0213756 A1 | 10/2004 | Michal et al. |
| 2004/0229856 A1 | 11/2004 | Chandrasekar et al. |
| 2005/0015048 A1 | 1/2005 | Chiu |
| 2005/0031874 A1 | 2/2005 | Michal et al. |
| 2005/0042254 A1 | 2/2005 | Freyman et al. |
| 2005/0064038 A1 | 3/2005 | Dinh et al. |
| 2005/0065281 A1 | 3/2005 | Lutolf et al. |
| 2005/0070844 A1 | 3/2005 | Chow et al. |
| 2005/0186240 A1 | 8/2005 | Ringeisen et al. |
| 2005/0281883 A1 | 12/2005 | Daniloff et al. |
| 2006/0149392 A1 | 7/2006 | Hsieh et al. |
| 2006/0233850 A1 | 10/2006 | Michal |
| 2007/0270948 A1 | 11/2007 | Wuh |
| 2008/0025943 A1 | 1/2008 | Michal et al. |
| 2012/0225040 A1 | 9/2012 | Hossainy et al. |
| 2012/0225041 A1 | 9/2012 | Hossainy et al. |

FOREIGN PATENT DOCUMENTS

| | | |
|---|---|---|
| EP | 0938871 | 9/1999 |
| EP | 1214077 | 1/2004 |
| FR | 2715855 | 8/1995 |
| GB | 2194144 | 3/1988 |
| JP | 61205446 | 9/1986 |
| JP | 06507106 | 8/1994 |
| JP | 10236984 | 9/1998 |
| JP | 3063935 | 12/1999 |
| JP | 2000502380 | 2/2000 |
| JP | 2000262525 | 9/2000 |
| JP | 2003062089 | 3/2003 |
| JP | 2007009185 | 1/2007 |
| JP | 2006523507 | 10/2009 |
| WO | WO-9210142 | 6/1992 |
| WO | WO-9315781 | 8/1993 |
| WO | WO-9830207 | 7/1998 |
| WO | WO-9854301 | 12/1998 |
| WO | WO-9953943 | 10/1999 |
| WO | WO-0016818 | 3/2000 |
| WO | WO-0054661 | 9/2000 |
| WO | WO-0071196 | 11/2000 |
| WO | WO-0124775 | 4/2001 |
| WO | WO 0124842 | 4/2001 |
| WO | WO-0145548 | 6/2001 |
| WO | WO-0149357 | 7/2001 |
| WO | WO-0200173 | 1/2002 |
| WO | WO-0204008 | 1/2002 |
| WO | WO-0228450 | 4/2002 |
| WO | WO-0240070 | 5/2002 |
| WO | WO-02072166 | 9/2002 |
| WO | WO-02087623 | 11/2002 |
| WO | WO-03022324 | 3/2003 |
| WO | WO-03022909 | 3/2003 |
| WO | WO-03026492 | 4/2003 |
| WO | WO-03027234 | 4/2003 |
| WO | WO-03064637 | 8/2003 |
| WO | WO-04000915 | 12/2003 |
| WO | WO-2004050013 | 6/2004 |
| WO | WO-2004058305 | 7/2004 |
| WO | WO-2004060346 | 7/2004 |
| WO | WO-2004066829 | 8/2004 |
| WO | WO-2004091592 | 10/2004 |
| WO | WO-2004098669 | 11/2004 |
| WO | WO-2005061019 | 7/2005 |

| WO | WO-2005067890 | 7/2005 |
| WO | WO-2006027549 | 3/2006 |
| WO | WO-2006039704 | 4/2006 |
| WO | WO-2006113407 | 10/2006 |
| WO | WO-2007048831 | 3/2007 |
| WO | WO-2007145909 | 12/2007 |

OTHER PUBLICATIONS

Mogan C, Larson DF. "Rationale of platelet gel to augment adaptive remodeling of the injured heart." J Extra Corpor Technol. Jun. 2004;36(2):191-6.*

Michael E. Davis; J.P. Michael Motion; Daria A. Narmoneva; Tomosaburo Takahashi; Daihiko Hakuno; Roger D. Kamm; Shuguang Zhang; Richard T. Lee "Injectable Self-Assembling Peptide Nanofibers Create Intramyocardial Microenvironments for Endothelial Cells" Circulation, 2005, 111, pp. 442-450.*

Abbot Cardiovascular Systems, Non final office action dated Aug. 13, 2010 for U.S. Appl. No. 11/447,340.

Abbot Cardiovascular Systems, Final office action mailed Sep. 27, 2010 for U.S. Appl. No. 10/792,960.

Abbot Cardiovascular Systems, Final office action mailed Sep. 27, 2010 for U.S. Appl. No. 12/016,180.

Abbot Cardiovascular Systems, Final Office Action mailed Nov. 22, 2010 for U.S. Appl. No. 10/781,984, 13 pages.

Abbot Cardiovascular Systems, Non-final Office Action mailed Nov. 24, 2010 for U.S. Appl. No. 12/013,286, 11 pages.

Abbot Cardiovascular Systems, Non-final Office Action mailed Dec. 8, 2010 for U.S. Appl. No. 11/566,643, 17 pages.

Abbot Cardiovascular Systems, Non-final Office Action mailed Dec. 10, 2010 for U.S. Appl. No. 11/938,752, 32 pages.

Abbot Cardiovascular Systems, Non-final Office Action mailed Dec. 17, 2010 for U.S. Appl. No. 11/933,922, 23 pages.

Abbott Cardiovascular Systems, *website for Healon (R) OVD*, copyright 2010, accessed Dec. 15, 2010, URL: <http://abbottmedicaloptics.com/products/cataract/ovds/healon-viscoelastic>, (2010), 2 pages.

Abbott Cardiovascular Systems, *Product Information Sheet for Healon (R), from Abbott Medical Optics*, (2005), 1 page.

Abbott Cardiovascular Systems, Japanese Office Action dated Dec. 8, 2010 for Japanese Patent App No. 2006-509975., 6 pages.

Abbott Cardiovascular Systems, Non final office action mailed Feb. 8, 2011 for U.S. Appl. No. 10/792,960.

Haynesworth, Stephen E., et al., "Platelet Effects on Human Mesenchymal Stem Cells", *Abstract, presented at Orthopaedic Research Society 48th Annual Meeting*, Dallas, TX, (Feb. 10-13, 2010), 2 pages.

Abbott Cardiovascular Systems, Non final office action mailed Jul. 6, 2011 for U.S. Appl. No. 10/781,984.

Abbott Cardiovascular Systems, Final office action mailed Jun. 28, 2011 for U.S. Appl. No. 10/792,960.

Abbott Cardiovascular Systems, Final office action mailed Jul. 18, 2011 for U.S. Appl. No. 11/566,643.

Abbott Cardiovascular Systems, Non-Final office action mailed Aug. 31, 2011 for U.S. Appl. No. 11/110,223.

Abbott Cardiovascular Systems, Final office action mailed Sep. 20, 2011 for U.S. Appl. No. 11/938,752.

Abbott Cardiovascular Systems, Final Office Action mailed Oct. 21, 2011 for U.S. Appl. No. 10/781,984, 10 pages.

Abbott Cardiovascular Systems, Non final office action mailed Nov. 8, 2011 for U.S. Appl. No. 10/792,960.

Abbott Cardiovascular Systems, Final Office Action mailed Jan. 5, 2012 for U.S. Appl. No. 11/361,920, 13 pages.

Abbott Cardiovascular Systems, Office Action mailed Jan. 17, 2012 for European Patent Application 08727952.7, 6 pages.

Abbott Cardiovascular Systems, Non-Final Office Action mailed Jan. 30, 2012 for U.S. Appl. No. 10/781,984, 10 pages.

Abbott Cardiovascular Systems, Final Office Action mailed Feb. 8, 2012 for Japanese application No. 2006-509975, 6 pages.

Abbott Cardiovascular Systems, Non-Final Office Action mailed Feb. 15, 2012 for U.S. Appl. No. 12/114,717, 16 pages.

Abbott Cardiovascular Systems, Final Office Action mailed Apr. 4, 2012 for U.S. Appl. No. 10/792,960, 13 pages.

Abbott Cardiovascular Systems, European Office Action mailed Apr. 11, 2012 for App No. 12155231.9, 9 pages.

Abbott Cardiovascular Systems, European Office Action mailed Apr. 10, 2012 for App No. 07810637.4, 6 pages.

Abbott Cardiovascular Systems, Non Final Office Action dated May 12, 2009 for U.S. Appl. No. 11/496,824.

Abbott Cardiovascular Systems, Non Final Office Action dated Mar. 13, 2009 for U.S. Appl. No. 10/414,602.

Abbott Cardiovascular Systems, International search report and written opinion datd Jun. 18, 2009 for PCT/US2008/051505.

Abbott Cardiovascular Systems, Non final office action dated Jul. 9, 2009 for U.S. Appl. No. 11/561,328.

Abbott Cardiovascular Systems, International Preliminary Report on Patentability dated Jul. 30, 2009 for PCT/US2008/051505.

Abbott Cardiovascular Systems, Final office action dated Nov. 12, 2009 for U.S. Appl. No. 12/013,286.

Abbott Cardiovascular Systems, Final office action dated Nov. 25, 2009 for U.S. Appl. No. 11/566,643.

Abbott Cardiovascular Systems, Non final office action dated Dec. 9, 2009 for U.S. Appl. No. 10/781,984.

Abbott Cardiovascular Systems, Examination Report dated Jan. 13, 2010 for EP Application No. 07795729.8.

Abbott Cardiovascular Systems, Non final office action dated Feb. 5, 2010 for U.S. Appl. No. 11/447,340.

Abbott Cardiovascular Systems, Final Office Action dated Jan. 29, 2010 for U.S. Appl. No. 10/792,960.

Abbott Cardiovascular Systems, Examination Report dated Jan. 15, 2010 for EP 08727952.7.

Abbott Cardiovascular Systems, Examination Report dated Feb. 5, 2010 for EP 07810637.4.

Abbott Cardiovascular Systems, Office Action dated Apr. 6, 2009 for U.S. Appl. No. 11/447,340.

Abbott Cardiovascular Systems, Office Action dated Mar. 30, 2009 for U.S. Appl. No. 10/792,960.

Abbott Cardiovascular Systems, Office Action dated Apr. 13, 2009 for U.S. Appl. No. 11/566,643.

Abbott Cardiovascular Systems, Office Action dated Apr. 29, 2009 for U.S. Appl. No. 12/013,286.

Abbott Cardiovascular Systems in, PCT Search Report and Written Opinion dated Aug. 26, 2008 for PCT/US2007/016433.

Abbott Cardiovascular Systems in, PCT Search Report and Written Opinion dated Jul. 31, 2008 for PCT/US2007/024158.

Abbott Cardiovascular Systems in, PCT International Preliminary Report on Patentability and Written Opinion dated Dec. 24, 2008 for PCT/US2007/013181.

Abbott Cardiovascular Systems in, "PCT International Search Report and Written Opinion mailed Feb. 10, 2009", PCT/US2007/023419.

Abbott Cardiovascular Systems in, "PCT Search Report dated Feb. 12, 2008", PCT Appln No. PCT/US2007/013181.

Abbott Cardiovascular Systems in, "PCT Search Report dated Jan. 31, 2007", PCT Appln No. PCT/US2006/014021.

Abbott Cardiovascular Systems in, "PCT Search Report dated Mar. 27, 2008", PCT Appln No. PCT/US2007/003614.

Advanced Cardiovascular Systems, Inc., et al., "PCT International Preliminary Report on Patentability dated Jun. 19, 2007", PCT Appln. No. PCT/US2005/045627.

Advanced Cardiovascular Systems, Inc., "PCT International Preliminary Report on Patentability dated Nov. 3, 2005", PCT Appln. No. PCT/US2004/011356.

Advanced Cardiovascular Systems, Inc., "PCT International Search Report and Written Opinion mailed Oct. 13, 2006", for. PCT/US2005/045627.

Advanced Cardiovascular Systems, Inc., "PCT International Search Report dated Feb. 9, 2004", PCT Appln. No. PCT/US03/30464.

Advanced Cardiovascular Systems, Inc., "PCT International Search Report dated Jan. 28, 2004", PCT Appln. No. PCT/US03/18360.

Advanced Cardiovascular Systems, Inc., "PCT Invitation to Pay Additional Fees mailed Nov. 4, 2003", PCT Appln No. PCT/US03/18360.

Advanced Cardiovascular Systems, Inc., "PCT Search Report and Written Opinion dated Nov. 24, 2004", PCT Appln. No. PCT/US2004/011356.

Agocha, A., et al., "Hypoxia regulates basal and induced DNA synthesis and collagen type I production in human cardiac fibroblasts: effects of transforming growth factor-beta 1, thyroid hormone, angiotensin II and basic fibroblast growth factor", J. Mol. Cell. Cardiol., 29(8), (Apr. 1997), pp. 2233-2244.

Allemann, E., et al., "Kinetics of Blood Component Adsorption on poly(D,L-lactic acid) Nanoparticles: Evidence of Complement C3 Component Involvement", J. Biomed. Mater. Res., 37(2), Abstract downloaded from the Internet at www.ncbi.nlm.nih.gov/entrez/query.fcgi?cmd=Retrieve&db=PubMed, (Nov. 1997), pp. 229-234.

Anderson, James M., et al., "Biodegradation and biocompatibility of PLA and PLGA microspheres", Advanced Drug Delivery Reviews 28, (1997), 5-24.

Assmus, B., et al., "Transplantation of Progenitor Cells and Regeneration Enhancement in Acute Myocardial Infarction (TOPCARE-AMI)", Clinical Investigation and Reports, Circulation, 106, (2002), 3009-3017.

Baxter, "FloSeal Matrix Hemostatic Sealant", downloaded from the Internet on Nov. 14, 2002, from: http://www.fusionmed.com/docs/surgeon/default.asp.

Berger, et al., "Poly-L-cysteine", J. Am. Chem. Soc., 78(17), (Sep. 5, 1956), pp. 4483-4488.

Bernatowicz, M., et al., "Preparation of Boc-[S-(3-nitro-2-pyridinesulfenyl)]-cysteine and its use for Unsymmetrical Disulfide Bond Formation", Int. J. Peptide Protein Res. 28(2), (Aug. 1996), pp. 107-112.

Boland, E. D., "Electrospinning Collagen and Elastin: Preliminary Vascular Tissue Engineering", Frontiers in Bioscience, vol. 9, (May 1, 2004), pp. 1422-1432.

Brust, G., "Polyimides", downloaded from the Internet at: http://www.pslc.ws/macrog/imide.htm, (2005), 4 pages.

Buschmann, I , et al., "Arteriogenesis versus angiogenesis: Two mechanisms of vessel growth", News Physiol. Sci., vol. 14, (Jun. 1999), 121-125.

Canderm Pharma, "Technical Dossier: Artecoll", downloaded from the Internet on Oct. 22, 2002 from: http://www.canderm.com/artecoll/tech.html, 3 pages.

Capan, Y., et al., "Preparation and Characterization of Poly(D,L-lactide-co-glycolide) Microspheres for Controlled Release of Human Growth Hormone", AAPS PharmSciTech.; 4(2): article 28, Downloaded from the Internet at: http://www.aapspharmscitech.org/view.asp?art=pt040228&pdf=yes, (2003), 12 pages.

Caplan, Michael J., et al., "Dependence on pH of polarized sorting of secreted proteins", Nature, vol. 29, (Oct. 15, 1987), 630.

Carpino, L., et al., "Tris(2-aminoethyl)amine as a Substitute for 4-(Aminomethyl)piperidine in the FMOC/Polyamine Approach to Rapid Peptide Synthesis", J. Org. Chem., 55(5), (Mar. 1990), pp. 1673-1675.

Chandy, et al., "The development of porous alginate/elastin/PEG composite matrix for cardiovascular engineering", Journal of Biomaterials Applications, vol. 17, (Apr. 2003), 287-301.

Choi, Young Seon , et al., "Study on gelatin-containing artificial skin: I. Preparation and characteristics of novel gelatin-alginate sponge", Biomaterials, vol. 20, (1999), 409-417.

Corbett, S., et al., "Covalent Cross-linking of Fibronectin to Fibrin is Required for Maximal Cell Adhesion to a Fibronectin-Fibrin Matrix", The Journal of Biological Chemistry, 272(40), (Oct. 3, 1997), pp. 24999-25005.

Creemers, E., et al., "Matrix Metalloproteinase Inhibition After Myocardial Infarction: A New Approach to Prevent Heart Failure?", Circ. Res., vol. 89, (2001), pp. 201-210.

Crivello, et al., "Synthesis and Photoinitiated Cationic Polymerization of Monomers with the Silsesquioxane Core", J Polym Science: Part A: Polymer Chemistry 35, (1997), pp. 407-425.

Davis, M. E., et al., "Injectable Self-Assembling Peptide Nanofibers Create Intramyocardial Microenvironments for Endothelial Cells", Circulation, 111, (Feb. 2005), pp. 442-450.

De Rosa, et al., "Biodegradable Microparticles for the Controlled Delivery of Oligonucleotides", International Journal of Pharmaceutics, 242, (Aug. 21, 2002), pp. 225-228.

Desai, M., et al., "Polymer bound EDC (P-EDC): A convenient reagent for formation of an amide bond", Tetrahedron Letters, 34(48), Abstract downloaded from the Internet at www.sciencedirect.com, 1 page, (Nov. 1993), pp. 7685-7688.

Dinbergs, et al., "Cellular response to transforming growth factor-β1 and basic fibroblast growth factor depends on release kinetics and extracellular matrix interactions", The Journal of Biological Chemistry, vol. 271, No. 47, (Nov. 1996), 29822-29829.

Dong, Zhanfeng, et al., "Alginate/gelatin blend films and their properties for drug controlled release", Journal of Membrane Science, vol. 280, (2006), 37-44.

Edelman, "Controlled and modulated release of basic fibroblast growth factor", Biomaterials, vol. 12, (Sep. 1999), 619-626.

Elbert, D. L., et al., "Protein delivery from materials formed by self-selective conjugate addition reactions", Journal of Controlled Release, 76, (2001), 11-25.

Etzion, S., et al., "Influence of Embryonic Cardiomyocyte Transplantation on the Progression of Heart Failure in a Rat Model of Extensive Myocardial Infarction", J. Mol. Cell Cardiol., 33, (May 2001), pp. 1321-1330.

Ferrara, N., "Role of Vascular Endothelial Growth Factor in the Regulation of Angiogenesis", Kidney International, 56(3), Abstract downloaded from the Internet at www.nature.com/ki/journal/v56/n3/abs/4490967a.html, (1999), pp. 794-814.

Friedman, Paul M., et al., "Safety Data of Injectable Nonanimal Stabilized Hyaluronic Acid Gel for Soft Tissue Augmentation", Dermatologic Surgery, vol. 28, (2002), pp. 491-494.

Fuchs, S. , et al., "Catheter-Based Autologous Bone Marrow Myocardial Injection in No-Option Patients with Advanced Coronary Artery Disease", J. Am. Coll. Cardiol., 41(10), (2003), pp. 1721-1724.

Fukumoto, S., et al., "Protein Kinase C δ Inhibits the Proliferation of Vascular Smooth Muscle Cells by Suppressing G1 Cyclin Expression", The Journal of Biological Chemistry, 272(21), (May 1997), pp. 13816-13822.

Giordano, F., et al., "Angiogenesis: The Role of the Microenvironment in Flipping the Switch", Current Opinion in Genetics and Development, 11, (2001), pp. 35-40.

Gossler, et al., "Transgenesis by means of blastocyst-derived embryonic stem cell lines", Proc. Natl. Acad. Sci. USA, 83, (Dec. 1986), pp. 9065-9069.

Grafe, T. H., "Nanofiber Webs from Electrospinning", Presented at the Nonwovens in Filtration—Fifth International Conference Stuttgart, Germany, (Mar. 2003), pp. 1-5.

Gref, R., et al., "Biodegradable Long-Circulating Polymeric Nanospheres", Science, 263(5153), Abstract downloaded from the Internet at: http://www.sciencemag.org/cgi/content/abstract/263/5153/1600, 1 page, (Mar. 1994), pp. 1600-1603.

Grund, F., et al., "Microembolization in Pigs: Effects on Coronary Blood Flow and Myocardial Ischemic Tolerance", Am. J. Physiol., 277 (Heart Circ. Physiol. 46), (1999), pp. H533-H542.

Gupta, et al., "Changes in Passive Mechanical Stiffness of Myocardial Tissue with Aneurysm Formation", Circulation, 89(5), (May 1994), pp. 2315-2326.

Hanawa, T., et al., "New oral dosage form for elderly patients: preparation and characterization of silk fibroin gel", Chemical and Pharmaceutical Bulletin, Pharmaceutical Society of Japan, Tokyo, vol. 43, No. 2, (Jan. 1995), 284-288.

Hashimoto, T., et al., "Development of Alginate Wound Dressings Linked with Hybrid Peptides Derived from Laminin and Elastin", Biomaterials, 25, (2004), pp. 1407-1414.

Haugland, et al., "Dialkylcarbocyanine and Dialkylaminostryryl Probes", Handbook of Fluorescent Probes and Research Products, Molecular Probes, Inc., (2002), 530-534.

Haugland, et al., "Membrane-permeant reactive tracers", Handbook of Fluorescent Probes and Research Products, Molecular Probes, Inc., (2002), 458-553.

Heeschen, C., et al., "Nicotine Stimulates Tumor Angiogenesis", American College of Cardiology, 37(2) Supplement A,, Abstract downloaded from the Internet at: http://24.132.160.238/ciw-01acc/abstract_search_author.cfm?SearchName=Heeschen, 1 page, (Feb. 2001), pp. 1A-648A.

Helisch, A., et al., "Angiogenesis and arteriogenesis", NEUE Diagnostische Und Therap. Verfahren, Z Kardiol 89, (2000), 239-244.

Hendel, R. C., et al., "Effect of Intracoronary Recombinant Human Vascular Endothelial Growth Factor on Myocardial Perfusion: Evidence for a Dose-Dependent Effect", Circulation, 101, (2000), pp. 118-121.

Henry, R. R., et al., "Insulin Action and Glucose Metabolism in Nondiabetic Control and NIDDM Subjects: Comparison Using Human Skeletal Muscle Cell Cultures", Diabetes, 44(8), Abstract downloaded from the Internet at www.diabetes.diabetesjournals.org/cgi/content/abstract/44/8/936, (1995), pp. 936-946.

Hoffman, "Hydrogels for Biomedical Applications", Advanced Drug Delivery Reviews, vol. 43, (2002), pp. 3-12.

Holland, N. B., et al., "Biomimetic Engineering of Non-Adhesive glycocalyx-like Surfaces Using Oligosaccharide Surfactant Polymers", Nature, 392, Abstract downloaded from the Internet at www.nature.com, (Apr. 1998), pp. 799-801.

Horan, R.L., et al., "In Vitro Degradation of Silk Fibroin", Biomaterials, vol. 26, (2004), 3385-3393.

Hovinen, J., et al., "Synthesis of 3'-functionalized oligonucleotides on a single solid support", Tetrahedron Letters, 34(50), Abstract downloaded from the Internet at www.sciencedirect.com, (Dec. 1993), pp. 8169-8172.

Huang, K., et al., "Synthesis and Characterization of Self-Assembling Block Copolymers Containing Bioadhesive End Groups", Biomacromolecules, 3(2), (2002), pp. 397-406.

Hutcheson, K., et al., "Comparison of Benefits on Myocardial Performance of Cellular Cardiomyoplasty with Skeletal Myoblasts and Fibroblasts", Cell Transplantation, 9(3), (2000), pp. 359-368.

Huynh, T. V., et al., "Constructing and Screening cDNA Libraries in λgt10 and λgt11", Chapter 2 in DNA Cloning, vol. 1: A Practical Approach, ed. By D.M. Glover, (1985), pp. 49-78.

Indik, Z., et al., "Production of Recombinant Human Tropoelastin: Characterization and Demonstration of Immunologic and Chemotactic Activity", Arch. Biochem. Biophys., 280(1), Abstract downloaded from the Internet at: http://www.ncbi.nlm.nih.gov/entrez/query.fcgi?cmd=Retrieve&db=PubMed, 1 page, (Jul. 1990), pp. 80-86.

Iskandrian, A. S., et al., "Nuclear Cardiac Imaging: Principles and Applications", second edition, F.A. Davis Co., Philadelphia, cover page, title page and TOC, (1996), 5 pages total.

Isner, J. M., "Vascular Endothelial Growth Factor: Gene Therapy and Therapeutic Angiogenesis", Am. J. Cardiol., 82(10A), (Nov. 19, 1998), pp. 63S-64S.

Ito, Wulf D., et al., "Monocyte chemotactic protein-1 increases collateral and peripheral conductance after femoral artery occlusion", Max-Planck-Institute for Physiological and Clinical Research, Bad Nauheim, Germany, (Feb. 21, 1997), 829-837.

Johnson, et al., "The stabilization and encapsulation of human growth hormone nto biodegradable microspheres", Pharmaceutical Research, vol. 14, No. 6, (1997), 730-735.

Jonasson, P., et al., "Denatured states of human carbonic anhydrase II: an NMR study of hydrogen/deuterium exchange at tryptophan-indole-Hn sites", FEBS Letters, 445, (1999), pp. 361-365.

Kalltorp, Mia, et al., "Inflammatory cell recruitment, distribution, and chemiluminescence response at IgG precoated- and thiol functionalized gold surfaces", Swedish Biomaterials Consortium, Swedish Foundation for Strategic Research, (Apr. 9, 1999), 251-259.

Kaplan, D.L., et al., "Spiderless Spider Webs", Nature Biotechnology, vol. 20, (2002), 239-240.

Kawai, et al., "Accelerated tissue regeneration through incorporation of basic fibroblast growth factor-impregnated gelatin microspheres into artificial dermis", Biomaterials, 21(5), (Mar. 2002), 489-499.

Kawasuji, M., et al., "Therapeutic Angiogenesis with Intramyocardial Administration of Basic Fibroblast Growth Factor", Ann Thorac Surg, 69, Abstract downloaded from the Internet at www.ats.ctsnetjournals.org/cgi/content/abstract/69/4/1155, (2000), pp. 1155-1161.

Kelley, et al., "Restraining Infarct Expansion Preserves Left Ventricular Geometry and Function After Acute Anteroapical Infarction", Circulation, 99, (1999), pp. 135-142.

Kelly, E. B., "Advances in Mammalian and Stem Cell Cloning", Genetic Engineering News, vol. 23, No. 7, (Apr. 1, 2003), pp. 17-18 & 68.

Khademhosseini, et al., "Microscale Technologies for Tissue Engineering and Biology", PNAS, vol. 103, No. 8, (Feb. 21, 2006), pp. 2480-2487.

Kim, D., et al., "Glow Discharge Plasma Deposition (GDPD) Technique for the Local Controlled Delivery of Hirudin from Biomaterials", Pharmaceutical Research, 15(5), (1998), pp. 783-786.

Kim, Ung-Jin, et al., "Structure and Properties of Silk Hydrogels", Biomacromolecules, vol. 5(3), (2004), 786-792.

Kinart, et al., "Electrochemical Studies of 2-hydroxy-3-(3,4-dimethyl-9-oxo-9H-thioxanthen-2-yloxy)N,N,N-trimethyl-1-propanium chloride", J. Electroanal. Chem, 294, (1990), pp. 293-297.

Kipshidze, Nicholas, et al., "Therapeutic angiogenesis for critical limb ischemia to limit or avoid amputation", University of Wisconsin Medical School, The Journal of Invasive Cardiology, vol. 11, No. 1, (Jan. 1999), 25-28.

Klein, S., et al., "Fibroblast Growth Factors as Angiogenesis Factors: New Insights Into Their Mechanism of Action", Regulation of Angiogenesis, I.D. Goldberg and E.M. Rosen (eds.), 79, (1997), pp. 159-192.

Klugherz, Bruce D., et al., "Gene delivery from a DNA controlled-release stent in porcine coronary arteries", Nature Biotechnology, vol. 18, (Nov. 2000), 1181-1184.

Kohilas, K, et al., "Effect of prosthetic titanium wear debris on mitogen-induced monocyte and lymphoid activation", John Hopkins University, Dept. of Orthopaedic Surgery, (Apr. 1999), 95-103.

Kweon, H. Y., et al., "Preparation of semi-interpenetrating polymer networks composed of silk fibroin and poly(ethyleneglycol) macromer", Journal of Applied Polymer Science, John Wiley and Sons Inc., New York, NY, vol. 80, (Jan. 2001), 1848-1853.

Kwok, C., et al., "Design of Infection-Resistant Antibiotic-Releasing Polymers: I. Fabrication and Formulation", Journal of Controlled Release, 62, (1999), pp. 289-299.

Laboratory of Liposome Research, "Liposomes: General Properties", downloaded from the Internet on Feb. 9, 2006 at www.unizh.ch/onkwww/lipos.htm.

Laham, R. J., "Intrapericardial Delivery of Fibroblast Growth Factor-2 Induces Neovascularization in a Porcine Model of Chronic Myocardial Ischemia", J. Pharmacol Exper Therap, 292(2), (2000), pp. 795-802.

Leibovich, S. J., et al., "Macrophage-Induced Angiogenesis is Mediated by Tumour Necrosis Factor-α" Nature, vol. 329, (Oct. 15, 1987), pp. 630-632.

Leor, J., et al., "Bioengineered Cardiac Grafts—A New Approach to Repair the Infarcted Myocardium?", Circulation, 102[suppl III], (2000), pp. 111-56-111-61.

Leor, J., et al., "Gene Transfer and Cell Transplant: An Experimental Approach to Repair a 'Broken Heart'", Cardiovascular Research, 35, (1997), pp. 431-441.

Leroux, J. C., et al., "An Investigation on the Role of Plasma and Serum Opsonins on the Internalization of Biodegradable poly(D,L-lactic acid) Nanoparticles by Human Monocytes", Life Sci., 57(7), Abstract downloaded from the Internet at www.ncbi.nlm.nih.gov/entrez/query.fcgi?cmd=Retrieve&db=pubmed, (1995), pp. 695-703.

Lewin, B., "Repressor is Controlled by a Small Molecule Inducer", Genes VII, Oxford University Press, 7th ed., (2000), pp. 277-280.

Li, et al., "Cell Therapy to Repair Broken Hearts", Can. J. Cardiol., vol. 14, No. 5, (May 1998), pp. 735-744.

Li, W. W., et al., "Lessons to be Learned from Clinical Trials of Angiogenesis Modulators in Ischemic Diseases", Angiogenesis in Health & Disease: Basic Mechanisms and Clinical Applications, Rubanyi, G. (ed), Marcel Dekker, Inc. New York, (2000), Chapter 33.

Li, J., et al., "PR39, A Peptide Regulator of Angiogenesis", Nature Medicine, 6(1), (Jan. 2000), pp. 49-55.

Li., Y. Y., et al., "Differential Expression of Tissue Inhibitors of Metalloproteinases in the Failing Human Heart", Circulation, 98(17), (1998), pp. 1728-1734.

Lindsey, M., et al., "Selective Matrix Metalloproteinase Inhibition Reduces Left Ventricular Remodeling but does not Inhibit Angiogenesis after Myocardial Infarction", Circulation, 105(6), (2002), pp. 753-758.

Long, D. M., et al., "Self-Cleaving Catalytic RNA", FASEB Journal, 7, (1993), pp. 25-30.

Lopez, J. J., et al., "Angiogenic potential of perivascular delivered aFGF in a porcine model of chronic myocardial ischemia", The American Physiological Society, 0363-6135/98, (1998), H930-H936.

Lopez, J. J., et al., "VEGF Administration in Chronic Myocardial Ischemia in Pigs", Cardiovasc. Res., 40(2), Abstract downloaded from the Internet at: http://www.ncbi.nlm.nih.gov/entrez/query.fcgi?cmd=Retrieve&db=pubmed, 1 page, (1998), pp. 272-281.

Lu, L., et al., "Biodegradable Polymer Scaffolds for Cartilage Tissue Engineering", Clinical Orthopaedics and Related Research, Carl T. Brighton (ed.). No. 391S, (2001), pp. S251-S270.

Luo, Y., et al., "Cross-linked Hyaluronic Acid Hydrogel Films: New Biomaterials for Drug Delivery", Journal of Controlled Release, 69, (2000), pp. 169-184.

Lutolf, M, et al., "Synthesis and Physicochemical Characterization of End-Linked Poly(ethylene glycol)-co-peptide Hydrogels Formed by Michael-Type Addition", Biomacromolecules, vol. 4, (2003), 713-722.

Lyman, M. D., et al., "Characterization of the Formation of Interfacially Photopolymerized Thin Hydrogels in Contact with Arterial Tissue", Biomaterials, 17(3), (1996), pp. 359-364.

Mansour, S., et al., "Disruption of the proto-oncogene int-2 in mouse embryo-derived stem cells: a general strategy for targeting mutations to non-selectable genes", Nature, 336, (1988), pp. 348-352.

Martin, S. L., et al., "Total Synthesis and Expression in *Escherichia coli* of a Gene Encoding Human Tropoelastin", Gene, (1995), Abstract.

McDevitt, T., et al., "In vitro Generation of Differentiated Cardiac Myofibers on Micropatterned Laminin Surfaces", J. Biomed Mater Res., 60, (2002), pp. 472-479.

Meinel, L., et al., "The Inflammatory Responses to Silk Films In Vitro and In Vivo", Biomaterials, vol. 26, (2005), 147-155.

Narmoneva, D. A., et al., "Self-assembling short oligopeptides and the promotion of angiogenesis", Biomaterials, 26, (2005), pp. 4837-4846.

Nazarov, R., et al., "Porous 3-D Scaffolds from Regenerated Silk Fibroin", Biomacromolecules, vol. 5(3), (2004), 718-726.

Nguyen, K. T., et al., "Photopolymerizable Hydrogels for Tissue Engineering Applications", Biomaterials, 23, (2002), pp. 4307-4314.

Nikolic, S. D., et al., "New Angiogenic Implant Therapy Improves Function of the Ischemic Left Venticle", Supplement to Circulation; Abstracts From Scientific Sessions 2000, 102(18), (Oct. 2000), pp. II-689, Abstract 3331.

Nikolic, Serjan D., et al., "Novel means to improve coronary blood flow", Clinical Science, Abstracts from Scientific Sessions, (2000), II-689.

Nitinol Technical Information, "NiTi Smart Sheets", downloaded from the Internet on Dec. 10, 2002 at: http://www.sma-inc.com/information.html, 1 page.

Nose, et al., "A novel cadherin cell adhesion molecule: its expression patterns associated with implantation and organogenesis of mouse embryos", Journal of Cell Biology, vol. 103 (No. 6, Pt. 2), The Rockefeller University Press, (Dec. 1986), 2649-2658.

Ohyanagi, H., et al., "Kinetic Studies of Oxygen and Carbon Dioxide Transport into or from Perfluorochemical Particles", Proc. ISAO, vol. 1 (Artificial Organs vol. 2 (Suppl.)), (1977), pp. 90-92.

Ozbas, B., et al., "Salt-Triggered Peptide Folding and Consequent Self-Assembly into Hydrogels with Tunable Modulus", Macromolecules, 37(19), (2004), pp. 7331-7337.

Ozbas-Turan, S., "Controlled Release of Interleukin-2 from Chitosan Microspheres", Journal of Pharmaceutical Sciences, 91(5), (May 2002), pp. 1245-1251.

Palmiter, R., et al., "Germ-Line Transformation of Mice", Ann. Rev. Genet., 20, (1986), pp. 465-499.

Patrick, C. R., "Mixing and Solution Properties of Organofluorine Compounds", Preparation, Properties and Industrial Applications of Organofluorine Compounds, Chapter 10, R.E. Banks (ed.), 1st edition, Ellis-Horwood Ltd., Chichester:England, (1982), pp. 323-342.

Peattie, R. A., et al., "Stimulation of In Vivo Angiogenesis by Cytokine-Loaded Hyaluronic Acid Hydrogel Implants", Biomaterials, 25(14), Abstract downloaded from: www.sciencedirect.com, (Jun. 2004).

Penta, K., et al., "Dell Induces Integrin Signaling and Angiogenesis by Ligation of αVβ3", J. Biolog. Chem., 274(16), (Apr. 1999), pp. 11101-11109.

Perin, E. C., et al., "Transendocardial, Autologous Bone Marrow Cell Transplantation for Severe, Chronic, Ischemic Heart Failure", Circulation, (2003).

Pouzet, B., et al., "Is Skeletal Myoblast Transplantation Clinically Relevant in the Era of Angiotensin-Converting Enzyme Inhibitors?", Circulation, 104 [suppl I], (Sep. 2001), pp. I-223-I-228.

Prather, et al., "Nuclear Transplantation in Early Pig Embryos", Biol. Reprod., 41, (1989), pp. 414-418.

Prosci Incorporated, "ILPIP (CT) Peptide".

Quellec, P., et al., "Protein Encapsulation Within Polyethylene Glycol-coated Nanospheres. I. Physicochemical Characterization", J. Biomed. Mater. Res., 42(1), (1998)), Abstract.

Ramirez-Solis, R., et al., "Gene Targeting in Embryonic Stem Cells", Methods in Enzymology, 225, (1993), pp. 855-878.

Rowley, et al., "Alginate Hydrogels as Synthetic Extracelllular Matrix Materials", Biomaterials, 20(1), (1999), 45-53.

Sawhney, A. S., et al., "Bioerodible Hydrogels Based on Photopolymerized Poly(ethylene glycol)-co-poly(a-hydroxy acid) Diacrylate Macromers", Macromolecules, 26(4), (1993), pp. 581-587.

Sbaa-Ketata, E., et al., "Hyaluronan-Derived Oligosaccharides Enhance SDF-1-Dependent Chemotactic Effect on Peripheral Blood Hematopoietic CD34+ Cells", Stem Cells, 20(6), Letter to the Editor downloaded from the Internet at www.stemcells.alphamedpress.org/cgi/content/full/20/6/585, (2002), 585-587.

Segura, T, et al., "Crosslinked Hyaluronic Acid Hydrogels: A Strategy to Functionalize and Pattern", Biomaterials, vol. 26(4), (Feb. 2005), 359-371.

Segura, T, et al., "DNA delivery from hyaluronic acid-collagen hydrogels via a substrate-mediated approach", Biomaterials, vol. 26, (2005), 1575-1584.

Segura, T., et al., "Substrate-Mediated DNA Delivery: Role of the Cationic Polymer Structure and Extent of Modification", Journal of Controlled Release, 93, (2003), pp. 69-84.

Segura, T., et al., "Surface-Tethered DNA Complexes for Enhanced Gene Delivery", Bioconjugate Chem, 13(3), (2002), pp. 621-629.

Shibasaki, F., et al., "Suppression of Signalling Through Transcription Factor NF-AT by Interactions Between Calcineurin and Bcl-2", Nature, 386(6626), Abstract downloaded from the Internet at www.ncbi.nlm.nih.goy/entrez/query.fcgi?CMD=Text&DB=pubmed, (1997).

Shin, H., et al., "Attachment, Proliferation, and Migration of Marrow Stromal Osteoblsts Cultured on Biomimetic Hydrogels Modified with an Osteopontin-Derived Peptide", Biomaterials, 25, (2004), pp. 895-906.

Shin, H., et al., "In vivo bone and soft tissue response to injectable, biodegradable oligo(poly(ethylene glycol) fumarate) hydrogels", Biomaterials 24, Elseview Science Ltd., (3201-3211), 2003.

Shu, Z, et al., "Disulfide-crosslinked hyaluronan-gelatin hydrogel films: a covalent mimic of the extracellular matrix for in vitro cell growth", Biomaterials, vol. 24(21), (Sep. 2003), 3825-3834.

Shu, Zheng, et al., "In situ crosslinkable hyaluronan hydrogels for tissue engineering", Biomaterials, vol. 25, No. 7-8, (Mar. 2004), 1339-1348.

Simons, M., et al., "Clinical trials in coronary angiogenesis: Issues, problems, consensus, An expert panel summary", Angiogenesis Research Center, American Heart Association, Inc. (Sep. 12, 2000), 1-14.

Spenlehauer, G, et al., "In vitro and in vivo degradation of poly(D,L lactide/glycolide) type microspheres made by solvent evaporation method", Biomaterials, vol. 10, (Oct. 1989), 557-563.

Spinale, F. G., "Matrix Metalloproteinases—Regulation and Dysregulation in the Failing Heart", Circ. Res., 90, (2002), pp. 520-530.
Springer, M., et al., "Angiogenesis Monitored by Perfusion with a Space-Filling Microbead Suspension", Mol. Ther., 1(1), Abstract downloaded from the Internet at www.ncbi.nlm.nih.gov/entrez/query.fcgi?cmd=Retrieve&db=PubMed, (2000), pp. 82-87.
Staatz, WD, et al., "Identification of a tetrapeptide recognition sequence for the alpha 2 beta 1 integrin in collagen", Journal of Biological Chemistry, 1991, 266(12), pp. 7363-7367.
Storm, G., et al., "Surface Modification of Nanoparticles to Oppose Uptake by the Mononuclear Phagocyte System", Advanced Drug Delivery Reviews, 17(1), Abstract downloaded from the Internet at www.sciencedirect.com, (Oct. 1995), pp. 31-48.
Strauer, B. , et al., "Repair of Infarcted Myocardium by Autologous Intracoronary Mononuclear Bone Marrow Cell Transplantation in Humans", Circulation, 106, (2002), pp. 1913-1918.
Tybulewicz, V., et al., "Neonatal lethality and lymphopenia in mice with a homozygous disruption of the c-abl proto-oncogene", Cell, 65(7), Abstract downloaded from the Internet at www.sciencedirect.com, (Jun. 1991), pp. 1153-1163.
Unger, E. F., et al., "Effects of a Single Intracoronary Injection of Basic Fibroblast Growth Factor in Stable angina Pectoris", Am. J. Cardiol, 85(12), Abstract downloaded from the Internet at www.sciencedirect.com, (Jun. 2000), pp. 1414-1419.
Van Der Giessen, Willem J., et al., "Marked inflammatory sequelae to implantation of biodegradable and nonbiodegradable polymers in porcine coronary arteries", Dept. of Cardiology, Erasmus University Rotterdam, Circulation, vol. 94, No. 7, (Oct. 1, 1996), 1690-1697.
Van Luyn, M. J., et al., "Cardiac Tissue Engineering: Characteristics of in Unison Contracting Two- and Three-Dimensional Neonatal Rat Ventricle Cell (Co)-Cultures", Biomaterials, 23, (2002), pp. 4793-4801.
Vercruysse, K. P., et al., "Synthesis and in Vitro Degradation of New Polyvalent Hydrazide Cross-Linked Hydrogels of Hyaluronic Acid", Bioconjugate Chem, 8(5), Abstract downloaded from the Internet at pubs.acs.org/cgi-bin/abstract.cgi/bcches/1997/8/105/abs/bc9701095.html, (1997), pp. 686-694.
Visscher, G.E., et al., "Tissue response to biodegradable injectable microcapsules", Journal of Biomaterials Applications, vol. 2, (Jul. 1987), 118-119.
Vlodavsky, I., et al., "Extracellular Matrix-resident Basic Fibroblast Growth Factor: Implication for the Control of Angiogenesis", J. Cell Biochem, 45(2), Abstract downloaded from the Internet at www.ncbisilm.nih.gov/entrez/guery.fcgi?cmd=Retrieve&db=PubMed, (Feb. 1991), pp. 167-176.
Wang, M., et al., "Mechanical Properties of Electrospun Silk Fibers", Macromolecules, vol. 37(18), (2004), 6856-6864.
Wasielewski, "Ischamische Erkrankungen, Gefassneubildung anregen", Deutsche Apotheker Zeitung, vol. 140, No. 3, Stuttgart (DE), (Jan. 20, 2000), 232-233.
Wilensky, R., et al., "Direct intraarterial wall injection of microparticles via a catheter: a potential durg delivery strategy following angioplasty", American Heart Journal, 122, (1991), p. 1136.
Witzenbichler, B., et al., "Vascular Endothelial Growth Factor-C (VEGF-C/VEGF-2) Promotes Angiogenesis in the Setting of Tissue Ischemia", AM Pathol., 153(2), (Aug. 1998), pp. 381-394.
Yager, P., et al., "Silk Protein Project", www.faculty.washington.edu/yagerp/silkprojecthome.html, (Aug. 23, 1997).
Yamamoto, N., et al., "Histologic evidence that basic fibroblast growth factor enhances the angiogenic effects of transmyocardial laser revascularization", Basic Research in Cardiology, vol. 95, No. 1, (Feb. 1, 2000), 55-63.
Yeo, L.Y., et al., "AC Electrospray Biomaterials Synthesis", Biomaterials, (2005).
Zervas, L., et al., "On Cysteine and Cystine Peptides. II. S-Acylcysteines in Peptide Synthesis", J. Am. Chem. Soc., 85(9), (May 1963), pp. 1337-1341.
Zimmermann, W., et al., "Engineered Heart Tissue for Regeneration of Diseased Hearts", Biomaterials, 25, (2004), pp. 1639-1647.
Abbott Cardiovascular Systems, Final Office Action mailed Apr. 15, 2011 for U.S. Appl. No. 10/414,602.
Abbott Cardiovascular Systems, Non Final Office Action mailed Jun. 6, 2011 for U.S. Appl. No. 11/447,340.
Advanced Cardiovascular Systems, Extended European search report dated Apr. 21, 2011 for EP Application No. 10186186.2.
Advanced Cardiovascular Systems, Extended EP Search Report dated May 20, 2011 for EP Application No. 10186197.9.
Chung, Y. , et al., "Sol-gel transition temperature of PLGA-g-PEG aqueous solutions", Biomacromolecules, vol. 3, No. 3, (May 2002), 511-516.
Abbott Cardiovascular Systems, Final office action dated Apr. 22, 2010 for U.S. Appl. No. 10/414,602.
Abbott Cardiovascular Systems, Non final office action dated Apr. 29, 2010 for U.S. Appl. No. 10/792,960.
Abbott Cardiovascular Systems, Non-Final Office Action dated Jun. 4, 2010 for U.S. Appl. No. 10/781,984.
Abbott Cardiovascular Systems, Final Office Action Mailed Jun. 11, 2010 for U.S. Appl. No. 11/561,328.
Ritter, A. B., et al., "Elastic modulus, distensibility, and compliance (capacitance)", Biomedical Engineering Principles, Chapter 4, (2005), 187-191.
Abbott Cardiovascular Systems, Restriction requirement mailed Jul. 3, 2012 for U.S. Appl. No. 13/4722,324.
Abbott Cardiovascular Systems, Non-final Office Action mailed Aug. 28, 2012 for U.S. Appl. No. 13/472,324.
Abbott Cardiovascular Systems, Non-final Office Action mailed Aug. 30, 2012 for U.S. Appl. No. 13/472,328.
Abbott Cardiovascular Systems, Japanese Office Action dated Nov. 19, 2012 for Appln. No. 2009-539265.
Abbott Cardiovascular Systems, Japanese Office Action mailed Dec. 17, 2012 for JP Appln. No. 2009-546553.
Abbott Cardiovascular Systems, Non-Final Office Action dated Mar. 5, 2009 for U.S. Appl. No. 11/507,860.
Abbott Cardiovascular Systems, Non final office action dated Aug. 5, 2009 for U.S. Appl. No. 11/031,608.
Abbott Cardiovascular Systems, Final office action dated Mar. 29, 2010 for U.S. Appl. No. 11/031,608.
Abbott Cardiovascular Systems, Final Office Action mailed Jul. 15, 2010, U.S. Appl. No. 11/507,860.
Abbott Cardiovascular Systems, Final Office Action mailed Dec. 13, 2011 for U.S. Appl. No. 12/963,397.
Abbott Cardiovascular Systems, Final Office Action mailed May 9, 2012 for U.S. Appl. No. 11/110,223.
Abbott Cardiovascular Systems, European Search report for application No. 12151788.2 mailed Apr. 18, 2012, 6 pages.
Abbott Cardiovascular Systems, Non-final Office Action mailed Jun. 22, 2012 for U.S. Appl. No. 12/963,397.
Abbott Cardiovascular Systems, Non-final Office Action mailed Jun. 26, 2012 for U.S. Appl. No. 12/632,612.
Abbott Cardiovascular Systems, Japanese Office Action dated Jun. 11, 2012 for Appln. No. 2010-162711.
Abbott Cardiovascular Systems, Non-Final Office Action Sep. 11, 2012 for U.S. Appl. No. 10/792,960.
Abbott Cardiovascular Systems, Japanese office action dated Aug. 20, 2012 for JP 2009-537153.
Abbott Cardiovascular Systems, et al., Japanese Office Action dated Aug. 27, 2012 for JP 2009-522776.
Abbott Cardiovascular Systems, Final Office Action dated Nov. 8, 2012 for U.S. Appl. No. 12/114,717.
Abbott Cardiovascular Systems, Final Office Action mailed Nov. 7, 2012 for U.S. Appl. No. 10/781,984.
Bull, S., et al., "Self-Assembled Peptide Amphiphile Nanofibers Conjugated to MRI Contrast Agents", Nano Letters, vol. 5, No. 1, (Jan. 2005), 4 pages.
Csonka, E., et al., "Interspecific Interaction of Aortic Endothelial and Smooth Muscle Cells", Acta Morphologica Hungarica, vol. 35, No. 1-2, (1987), 31-35.
Griese, D. P., et al., "Vascular gene delivery of anticoagulants by transplantation of retrovirally-transduced endothelial progenitor cells", Cardiovascular Research, vol. 58, (2003), 469-477.

Hartgerink, J. D., et al., "Peptide-amphiphile nanofibers: A versatile scaffold for the preparation of self-assembling materials", PNAS, vol. 99, No. 8, (Apr. 16, 2002), 5133-5138.

Hartgerink, J. D., et al., "Self-Assembly and Mineralization of Peptide-Amphiphile Nanofibers", Science, vol. 294, (Nov. 23, 2001), 1684-1688.

Li, B., et al., "VEGF and PlGF promote adult vasculogenesis by enhancing EPC recruitment and vessel formation at the site of tumor neovascularization", The FASEB Journal, vol. 20, (2006), 1495-1497.

Seeger, J. M., et al., "Improved in vivo endothelialization of prosthetic grafts by surface modification with fibronectin", J Vasc Surg, vol. 8, No. 4, (Oct. 1988), 47682 (Abstract ony).

Urbich, C., et al., "Endothelial Progenitor Cells: Characterization and Role in Vascular Biology", Circulation Research, vol. 95, (2004), 343-353.

Zheng, W., "Mechanisms of coronary angiogenesis in response to stretch; role of VEGF and TGF-Beta", Am J Physiol Heart Circ Physiol 280(2), (Feb. 2001), H909-H917.

* cited by examiner

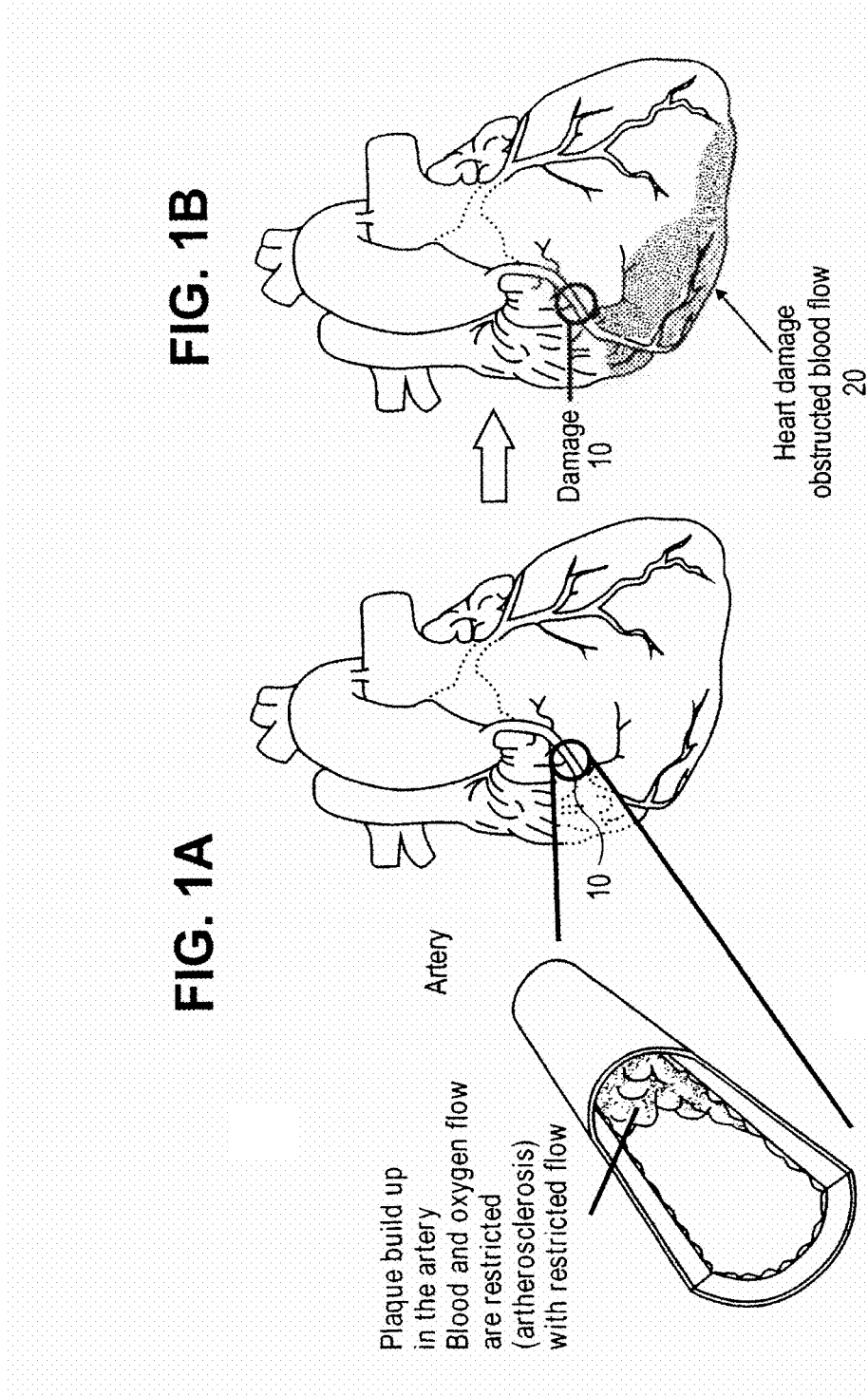

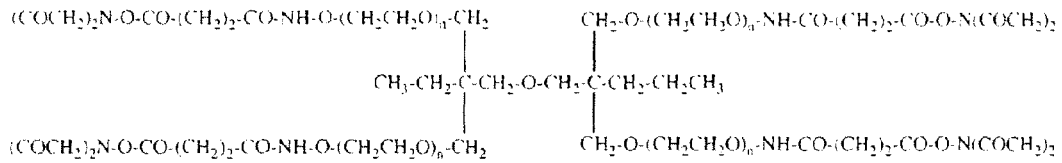
FIG. 2E
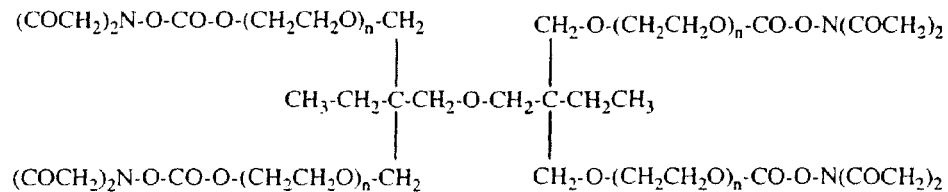
FIG. 2F
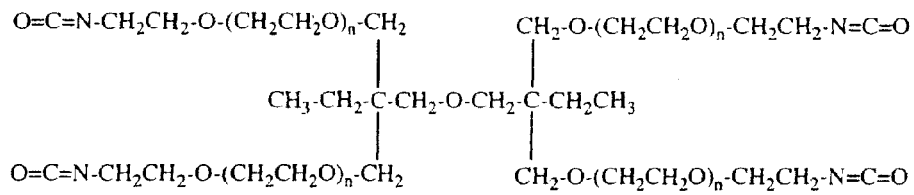
FIG. 2G
$(OCH_2CH_2)_n\text{-}X_m$
wherein $X = \text{-}NH_2, \text{-}SH, \text{-}OH, \text{-}PH_2, \text{-}CO\text{-}NH\text{-}NH_2$ and $m \geq 2$
FIG. 3

MODIFIED TWO-COMPONENT GELATION SYSTEMS, METHODS OF USE AND METHODS OF MANUFACTURE

CROSS-REFERENCE TO RELATED APPLICATION

The application is a divisional of co-pending U.S. patent application Ser. No. 11/496,824, filed Jul. 31, 2006 and incorporated herein by reference.

SEQUENCE LISTING

An electronic copy of the Sequence Listing entitled "P5130D2_ST25.txt" is herein incorporated by reference. This Sequence Listing consists of SEQ ID NOs. 1-3.

FIELD OF INVENTION

Post-myocardial infarction treatments and compositions.

BACKGROUND OF INVENTION

Ischemic heart disease typically results from an imbalance between the myocardial blood flow and the metabolic demand of the myocardium. Progressive atherosclerosis with increasing occlusion of coronary arteries leads to a reduction in coronary blood flow, which creates ischemic heart tissue. "Atherosclerosis" is a type of arteriosclerosis in which cells including smooth muscle cells and macrophages, fatty substances, cholesterol, cellular waste product, calcium and fibrin build up in the inner lining of a body vessel. "Arteriosclerosis" refers to the thickening and hardening of arteries. Blood flow can be further decreased by additional events such as changes in circulation that lead to hypoperfusion, vasospasm or thrombosis.

Myocardial infarction (MI) is one form of heart disease that results from the sudden lack of supply of oxygen and other nutrients. The lack of blood supply is a result of a closure of the coronary artery (or any other artery feeding the heart) which nourishes a particular part of the heart muscle. The cause of this event is generally attributed to arteriosclerosis in coronary vessels.

Formerly, it was believed that an MI was caused from a slow progression of closure from, for example, 95% then to 100%. However, an MI can also be a result of minor blockages where, for example, there is a rupture of the cholesterol plaque resulting in blood clotting within the artery. Thus, the flow of blood is blocked and downstream cellular damage occurs. This damage can cause irregular rhythms that can be fatal, even though the remaining muscle is strong enough to pump a sufficient amount of blood. As a result of this insult to the heart tissue, scar tissue tends to naturally form.

Various procedures, including mechanical and therapeutic agent application procedures, are known for reopening blocked arties. An example of a mechanical procedure includes balloon angioplasty with stenting, while an example of a therapeutic agent application includes administering a thrombolytic agent, such as urokinase. Such procedures do not, however, treat actual tissue damage to the heart. Other systemic drugs, such as ACE-inhibitors and Beta-blockers, may be effective in reducing cardiac load post-MI, although a significant portion of the population that experiences a major MI ultimately develop heart failure.

An important component in the progression to heart failure is remodeling of the heart due to mismatched mechanical forces between the infarcted region and the healthy tissue resulting in uneven stress and strain distribution in the left ventricle. Once an MI occurs, remodeling of the heart begins. The principle components of the remodeling event include myocyte death, edema and inflammation, followed by fibroblast infiltration and collagen deposition, and finally scar formation from extra-cellular matrix (ECM) deposition. The principle component of the scar is collagen which is non-contractile and causes strain on the heart with each beat. Non-contractility causes poor pump performance as seen by low ejection fraction (EF) and akinetic or diskinetic local wall motion. Low EF leads to high residual blood volume in the ventricle, causes additional wall stress and leads to eventual infarct expansion via scar stretching and thinning and border-zone cell apoptosis. In addition, the remote-zone thickens as a result of higher stress which impairs systolic pumping while the infarct region experiences significant thinning because mature myocytes of an adult are not regenerated. Myocyte loss is a major etiologic factor of wall thinning and chamber dilation that may ultimately lead to progression of cardiac myopathy. In other areas, remote regions experience hypertrophy (thickening) resulting in an overall enlargement of the left ventricle. This is the end result of the remodeling cascade. These changes also correlate with physiological changes that result in increase in blood pressure and worsening systolic and diastolic performance.

SUMMARY OF INVENTION

Compositions, methods of manufacture and methods of treatment for post-myocardial infarction are herein disclosed. In some embodiments, the composition includes at least two components. In one embodiment, a first component can include a first functionalized polymer and a substance having at least one cell adhesion site combined in a first buffer at a pH of approximately 6.5. A second component can include a second buffer in a pH of between about 7.5 and 9.0. A second functionalized polymer can be included in the first or second component. In some embodiments, the composition can include at least one cell type and/or at least one growth factor. In some embodiments, the composition(s) of the present invention can be delivered by a dual bore injection device to a treatment area, such as a post-myocardial infarct region.

BRIEF DESCRIPTION OF DRAWINGS

FIGS. 1A-1B illustrate the progression of heart damage once the build-up of plaque in an artery induces an infarct to occur.

FIGS. 2A-2G show examples of chemical structures of a functionalized polyethylene glycol.

FIG. 3 shows a general formula for the chemical structure of a functionalized polyethylene glycol.

DETAILED DESCRIPTION

Figure 2A:
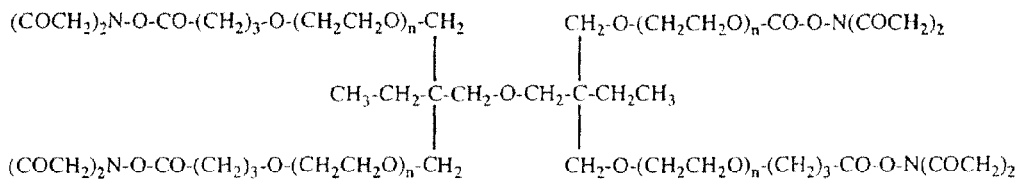
Figure 2B:
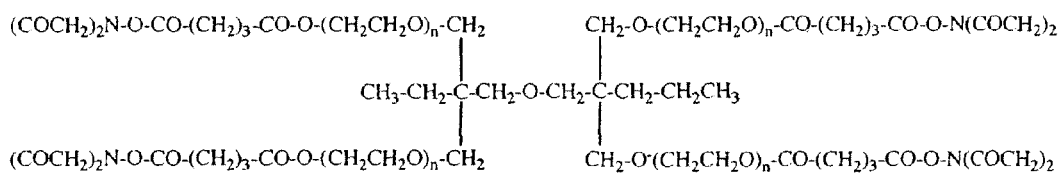
Figure 2C:
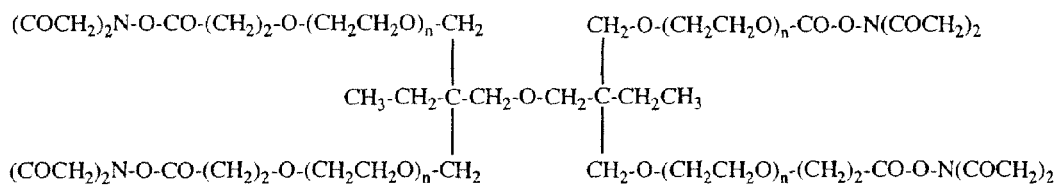
Figure 2D:
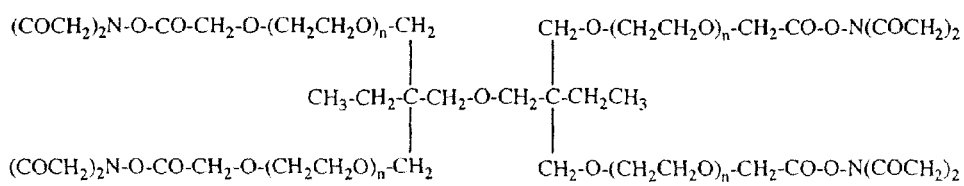

FIGS. 1A-1B illustrate the progression of heart damage once the build-up of plaque induces an infarct to occur. FIG. 1A illustrates a site 10 where blockage and restricted blood flow can occur from, for example, a thrombus or embolus. FIG. 1B illustrates resultant damage area 20 to the left ventricle that can result from the lack of oxygen and nutrient flow carried by the blood to the inferior region left of the heart. Damage area 20 will likely undergo remodeling, and eventually scarring, resulting in a non-functional area.

Bioscaffoldings formed of two components and applied in situ to the left heart ventricle can be used to treat post-myocardial infarction tissue damage. "Bioscaffolding" and "two-component gelation system" and "gelation system" are hereinafter used interchangeably. Examples of two-component gelation systems include, but are not limited to, alginate construct systems, fibrin glues and fibrin glue-like systems, self-assembled peptides, synthetic polymer systems and combinations thereof. Each component of the two-component gelation system may be co-injected to an infarct region by a dual-lumen delivery device. Examples of dual-lumen delivery devices include, but are not limited to, dual-needle left-ventricle injection devices, dual-needle transvascular wall injection devices and the like.

In some applications, the two-component gelation system includes fibrin glue. Fibrin glue consists of two main components, fibrinogen and thrombin. Fibrinogen is a plasma glycoprotein of about 340 kiloDaltons (kDa) in its endogenous state. Fibrinogen is a symmetrical dimer comprised of six paired polypeptide chains, alpha, beta and gamma chains. On the alpha and beta chains, there is a small peptide sequence called a fibrinopeptide which prevents fibrinogen from spontaneously forming polymers with itself. In some embodiments, fibrinogen is modified with proteins. Thrombin is a coagulation protein. When combined in equal volumes, thrombin converts the fibrinogen to fibrin by enzymatic action at a rate determined by the concentration of thrombin. The result is a biocompatible gel which gelates when combined at the infarct region. Fibrin glue can undergo gelation between about 5 to about 60 seconds. Examples of fibrin glue-like systems include, but are not limited to, Tisseel™ (Baxter), Beriplast P™ (Aventis Behring), Biocol® (LFB, France), Crosseal™ (Omrix Biopharmaceuticals, Ltd.), Hemaseel HMN® (Haemacure Corp.), Bolheal (Kaketsuken Pharma, Japan) and CoStasis® (Angiotech Pharmaceuticals).

In some applications, the two-component gelation system includes self-assembled peptides. Self-assembled peptides generally include repeat sequences of alternating hydrophobic and hydrophilic amino acid chains. The hydrophilic amino acids are generally charge-bearing and can be anionic, cationic or both. Examples of cationic amino acids are lysine and arginine. Examples of anionic amino acids are aspartic acid and glutamic acid. Examples of hydrophobic amino acids are alanine, valine, leucine, isoleucine or phenylalanine Self-assembled peptides can range from 8 to 40 amino acids in length and can assemble into nanoscale fibers under conditions of physiological pH and osmolarity. In sufficient concentration and over time, the fibers can assemble into an interconnected structure that appears macroscopically as a gel. Self-assembled peptides typically undergo gelation between several minutes to several hours. Examples of self-assembled peptides include, but are not limited to: AcN-RARADADARARADADA-CNH$_2$ (RAD 16-II), containing the sequence RARADADARARADADA (SEQ ID NO. 1); VKVKVKVKV-PP-TKVKVKVKV-NH$_2$ (MAX-1), containing the sequence VKVKVKVKV-PP-TKVKVKVKV (SEQ ID NO. 2); and AcN-AEAEAKAKAEAEAKAK-CNH$_2$ (EAK16-II), containing the sequence AEAEAKA-KAEAEAKAK (SEQ ID NO. 3); wherein Ac indicates acetylation, R is arginine, A is alanine, D is aspartic acid, V is valine, K is lysine, P is proline and E is glutamic acid.

In some applications, the two-component gelation system is an alginate construct system. One component may be an alginate conjugate (or alginate alone) which can include alginate and a protein constituent. The second component may be a salt. Examples of alginate conjugates can include, but are not limited to, alginate-collagen, alginate-laminin, alginate-elastin, alginate-collagen-laminin and alginate-hyaluronic acid in which the collagen, laminin, elastin, collagen-laminin or hyaluronic acid is covalently bonded (or not bonded) to alginate. Examples of salts which can be used to gel the alginate constructs include, but are not limited to, calcium chloride ($CaCl_2$), barium chloride ($BaCl_2$) or strontium chloride ($SrCl_2$).

In one embodiment, the alginate construct is alginate-gelatin. The molecular weight of the gelatin may be in the approximate range of 5 kDa to 100 kDa. The relatively low molecular weight of gelatin offers processing advantages in that it is more soluble and has lower viscosity than hydrogels of higher molecular weight. Another advantage of gelatin is that it contains from 1 to 4 RGD (arginine-glycine-aspartic acid peptide sequence) sites per molecule. RGD is a common cell adhesion ligand and would increase the retention of cells within the infarct zone where the bioscaffolding is formed. The cells retained by the RGD sites may be cells co-injected with the bioscaffolding components or dispersed throughout a component of the system.

The gelatin may be a porcine gelatin or a recombinant human gelatin. The porcine gelatin is a hydrolyzed type 1 collagen extracted from porcine skin. In one embodiment, the molecular weight of the porcine gelatin is approximately 20 kDa. The human gelatin is produced by bacteria using human genetic material. The human recombinant gelatin is equivalent to the porcine gelatin but may reduce the likelihood of an immune response when injected into an infarct region of a human subject.

Alginate is a linear polysaccharide derived from seaweed and contains mannuronic (M) and guluronic acid (G), presented in both alternating blocks and alternating individual residues. It is possible to use some of the carboxyl groups of the alginate as sites to graft useful cell adhesion ligands, such as collagen, laminin, elastin and other peptide fragments of the ECM matrix, forming an alginate conjugate, because alginate does not have RGD groups for cell attachment.

The alginate-gelatin conjugate can be formed of approximately 1% to 30% and more particularly approximately 10% to 20% gelatin (either porcine or human recombinant) and approximately 80% to 90% alginate. A relatively lower proportion of gelatin is used in the conjugate to retain gelation capacity of native alginate because the carboxyl groups of alginate that cause the gelation may be bound up in the alginate-gelatin conjugate.

In some embodiments, the two-component gelation system includes polyethylene glycols. PEG is a synthetic polymer having the repeating structure $(OCH_2CH_2)_n$. A first component may be a polyethylene glycol (PEG) polymer functionalized with at least two nucleophilic groups. Examples of nucleophilic groups include, but are not limited to, thiol (—SH), thiol anion (—S$^-$), and amine (—NH$_2$). A "nucleophile" is a reagent which is attracted to centers of positive charge. A nucleophile participates in a chemical reaction by donating electrons to an electrophile in order to form a chemical bond. A second component may be a PEG polymer functionalized with at least two electrophilic groups. Examples of electrophilic groups include, but are not limited to, N-hydroxy succinimide ester (—NHS), acrylate, vinyl sulfone, and maleimide. —NHS, or succinimidyl, is a five-member ring structure represented by the chemical formula —N(COCH$_2$)$_2$. An "electrophile" is a reagent attracted to electrons that participates in a chemical reaction by accepting an electron pair in order to bond to a nucleophile. The total number of electrophilic and nucleophilic groups should be greater than 4.

In some embodiments, two functionalized PEGs comprising a PEG functionalized with at least two nucleophilic groups and a PEG functionalized with at least two electrophilic groups can be combined in a 1:1 ratio. The PEGs can be stored in a 0.01M acidic solution at a pH below about 4.0. At room temperature and standard concentration, reaction and cross-linking between the two functionalized PEGs occurs beginning at approximately pH greater than 6.5. Under these conditions, reaction kinetics are slow. When 0.3 M basic buffer solution at pH about 9.0 is added to the PEGs, gelation occurs in less than 1 minute. This system exhibits poor cytocompatibility due to the low pH of the functionalized PEG solution and the high osmolality pH 9.0 buffer. "Cytocompatibility" refers to the ability of media to provide an environment conducive to cell growth. Additionally, this system does not include any cell adhesion sites.

Modified Polyethylene Glycol Gelation Systems

In some embodiments, a bioscaffolding is formed from combining functionalized polymers (bioscaffolding precursors) with an extra-cellular matrix (ECM) protein at physiological osmolality. The resulting bioscaffolding can be in a pH range of between about 6.5 and about 7.5. Examples of ECM proteins include, but are not limited to, collagen, laminin, elastin and fragments thereof, in addition to, proteins, protein fragments and peptides with cell adhesion ligands such as RGD groups. In some embodiments, cells can be added to the bioscaffolding precursors. Examples of cell types include, but are not limited to, localized cardiac progenitor cells, mesenchymal stem cells (osteoblasts, chondrocytes and fibroblasts), bone marrow derived mononuclear cells, adipose tissue derived stem cells, embryonic stem cells, umbilical-cord-blood-derived stem cells, smooth muscle cells or skeletal myoblasts. In some embodiments, growth factors can be added to the system. Examples of growth factors include, but are not limited to, isoforms of vasoendothelial growth factor (VEGF), fibroblast growth factor (FGF, e.g. beta-FGF), Del 1, hypoxia inducing factor (HIF 1-alpha), monocyte chemoattractant protein (MCP-1), nicotine, platelet derived growth factor (PDGF), insulin-like growth factor 1 (IGF-1), transforming growth factor (TGF alpha), hepatocyte growth factor (HGF), estrogens, follistatin, proliferin, prostaglandin E1 and E2, tumor necrosis factor (TNF-alpha), interleukin 8 (Il-8), hematopoietic growth factors, erythropoietin, granulocyte-colony stimulating factors (G-CSF) and platelet-derived endothelial growth factor (PD-ECGF).

The polymers can include synthetic polymers, such as polyamino acids, polysaccharides, polyalkylene oxide or polyethylene glycol (PEG). The molecular weight of the compounds can vary depending on the desired application. In most instances, the molecular weight (mol. wt.) is about 100 to about 100,000 mol. wt., and more preferably about 1,000 to about 20,000 mol. wt.

In some embodiments, the polymer is polyethylene glycol. As used herein, the term "polyethylene glycol(s)" includes modified and/or derivatized polyethylene glycols. According to some embodiments, a first functionalized PEG can be functionalized by at least two reactive groups, such as electrophilic groups. Examples of reactive groups include, but are not limited to, a succinimidyl group (—NHS), a vinyl group, such as acrylate, vinylsulfone, vinyl ether, allyl ether, vinyl ester, vinyl ketone or maleimide, and nitrophenolate or similar leaving group. According to some embodiments, a second functionalized PEG can be functionalized by at least two reactive groups, such as nucleophilic groups. Examples of reactive groups include, but are not limited to, a thiol group, an amino group, a hydroxyl group, phospine radical ($PH_2$) and —CO—NH—$NH_2$. Representative functionalized PEGs with electrophilic groups are shown in FIGS. 2A through 2G. A general representative formula for functionalized PEGs with nucleophilic groups is shown in FIG. 3. In some embodiments a PEG functionalized with electrophilic groups is combined with a PEG functionalized with nucleophilic groups to form a bioscaffolding gel. The total number of electrophilic and nucleophilic groups should be greater than 4.

The branched conformation of the PEGs represented in FIGS. 2A-2G & 3 is not limiting. In some embodiments, the combined functionality of the PEGs can be greater than four. "Functionality" refers to the number of electrophilic or nucleophilic groups on the polymer core that are capable of reacting with other nucleophilic or electrophilic groups, respectively, to form a gel. That is, as long as the PEGs to be combined are at least difunctional, i.e., each PEG contains at least two nucleophilic or electrophilic groups, the functionalized PEGs can be combined to form a bioscaffolding gel. The total number of electrophilic and nucleophilic groups should therefore be greater than 4.

In some embodiments, a bioscaffolding can include a first component with at least one functionalized PEG and an ECM protein, and a second component of buffer. "Component" hereinafter refers to one part of a two-part system and can include multiple constituents (e.g., a mixture). In one embodiment, the first component can include a mixture of a first functionalized PEG, such as —NHS PEG (or other functionalized PEG with at least two reactive groups), a second functionalized PEG, such as —SH PEG (or other functionalized PEG with at least two reactive groups), and an ECM protein. In some embodiments, the first component can include first functionalized polymer only, such as —NHS PEG (or other functionalized PEG with at least two reactive groups) and an ECM protein.

In some embodiments, the first functionalized PEG can be combined with the second functionalized PEG in a 1:1 ratio. In some embodiments, e.g., the functionalized PEGs can be combined in a ratio less than 1:1. For example, the two PEGs can have different number of functional groups and, as a result, the PEG stoichiometry could be altered. Alternatively, the crosslinking density may be altered by varying the polymer ratio. In some embodiments, the functionalized PEGs are combined in the solid phase. When preparing to deliver to a treatment site, the mixture can be suspended in a pH 6.5 buffer at approximately physiological osmolality, i.e., 280-300 mOsm/kg $H_2O$. Examples of buffers include, but are not limited to dilute hydrogen chloride and citrate buffers.

The second component can include a buffer in a pH range from approximately 7.5 to 9.5 at a concentration from about 140 mM to about 150 mM. Examples of buffers include sodium phosphate and sodium carbonate buffers. The buffer can be at approximately physiological osmolality, i.e., 280-300 mOsm/kg $H_2O$. In some embodiments, the second component can include an —SH PEG and the buffer (or other functionalized PEG with at least two reactive groups).

In some embodiments, a cell type can be added to the first component. Examples of cell types include, but are not limited to, localized cardiac progenitor cells, mesenchymal stem cells (osteoblasts, chondrocytes and fibroblasts), bone marrow derived mononuclear cells, adipose tissue derived stem cells, embryonic stem cells, umbilical-cord-blood-derived stem cells, smooth muscle cells or skeletal myoblasts. For example, human mesenchymal stem cells (hMSC) can be added to the first component. In some embodiments, a growth factor can be added to the first component. In some applications, the functionalized PEGs can react with the growth factors which could stabilize the growth factors, extend their half-life or provide a mode for controlled release of the growth factors. The growth factors can act to help survival of injected hMSC or endogenous progenitor cells at the infarct region. In addition, the growth factors can aid direct endogenous progenitor cells to the injury site.

In general, cells do not attach to PEG surfaces or gels formed from PEG polymers. That is, PEG polymers do not provide a cytocompatible environment for cells. Collagen or gelatin or any other ECM protein such as fibronectin, may be added to improve cytocompatibility. However, in the case of collagen, for example, the collagen added to the mixture of PEGs can make the mixture very viscous and therefore not conducive with catheter delivery systems. It is anticipated that the pH of the first component and the concentration of the second component, as described in embodiments of the invention, will increase the cytocompatibility of the cell types even with an ECM protein present.

In some embodiments, the first component can be combined with the second component to produce a bioscaffolding at an infarct region. When combined, the resulting bioscaffolding gel can be at a pH of between 6.8 and 7.4. Although the low buffer concentration of the second component may slow the reaction down, the resulting gel can enable improved cytocompatibility. The ECM protein can provide cell adhesion cites to enable cell spreading and migration. "Cell spreading" refers to the naturally occurring morphology that some cells attain when they are allowed to grow on cytocompatible surfaces. In the case of hMSC, the natural morphology is a flattened, spindle-shaped morphology. In some embodiments, the N-terminus and lysine and arginine side groups of the ECM may react with the —NHS PEG. This may provide better mechanical stability of the gel and reduce the tendency of the gel to swell. This reaction is what forms the gel.

In some embodiments, the —NHS group of the —NHS PEG can be replaced with a vinyl constituent such as acrylate, vinylsulfone, vinyl ketone, allyl ester, allyl ketone or maleimide group(s). When mixed with an —SH PEG at appropriate conditions, these groups can react with the thiol group(s) of the —SH PEG through a Michael type reaction. Michael type reactions are well known by those skilled in the art. In some embodiments, the reaction could be activated with a buffer in a pH range of between about 6.0 and about 9.0, by a catalytic amount of various amines or a combination thereof. It is anticipated that a Michael type reaction would contribute to the long term stability of the resulting gel since thioether bonds are formed as compared to the more hydrolytically labile thioester bonds formed from the reaction of thiols with activated esters. In some embodiments, the —NHS group of the —NHS PEG can be replaced with a leaving group such as a nitrophenolate.

In some embodiments, the —SH group of the —SH PEG can be replaced with an amino group to form an amide bond when combined with an —NHS or alternatively functionalized PEG.

Methods of Treatment

Devices which can be used to deliver each component of the gel include, but are not limited to, dual-needle left-ventricle injection devices, dual-needle transvascular wall injection and dual syringes. Methods of access to use the minimally invasive (i.e., percutaneous or endoscopic) injection devices include access via the femoral artery or the sub-xiphoid. "Xiphoid" or "xiphoid process" is a pointed cartilage attached to the lower end of the breastbone or sternum, the smallest and lowest division of the sternum. Both methods are known by those skilled in the art.

Figure 4:
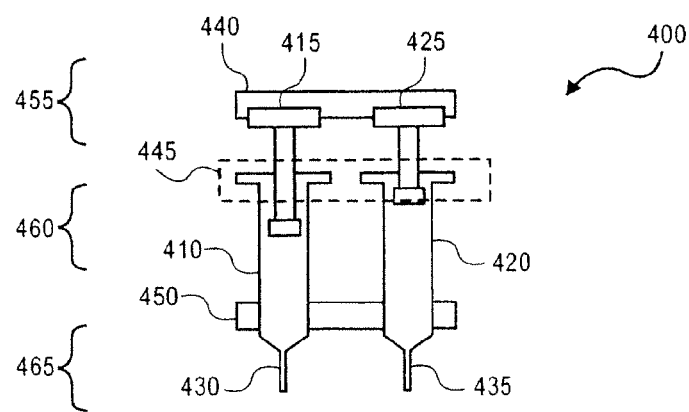
FIG. 4 illustrates an embodiment of a dual bore delivery device.

FIG. 4 illustrates an embodiment of a dual syringe device which can be used to deliver the compositions of the present invention. Dual syringe 400 can include first barrel 410 and second barrel 420 adjacent to one another and connected at a proximal end 455, distal end 460 and middle region 465 by plates 440, 445 and 450, respectively. In some embodiments, barrels 410 and 420 can be connected by less than three plates. Each barrel 410 and 420 includes plunger 415 and plunger 425, respectively. Barrels 410 and 420 can terminate at a distal end into needles 430 and 435, respectively, for extruding a substance. In some embodiments, barrels 410 and 420 can terminate into cannula protrusions for extruding a substance. Barrels 410 and 420 should be in close enough proximity to each other such that the substances in each respective barrel are capable of mixing with one another to form a bioscaffolding in the treatment area, e.g., a post-infarct myocardial region. Dual syringe 400 can be constructed of any metal or plastic which is minimally reactive or completely unreactive with the formulations described in the present invention. In some embodiments, dual syringe 400 includes a pre-mixing chamber attached to distal end 465.

In some applications, first barrel 410 can include a first component of a two-component polyethylene glycol gelation system and second barrel 420 can include a second component of the system according to any of the embodiments described previously. A therapeutic amount of the resulting gel is between about 25 μL to about 200 μL, preferably about 50 μL. Dual syringe 400 can be used during, for example, an open chest surgical procedure.

Figure 5A:
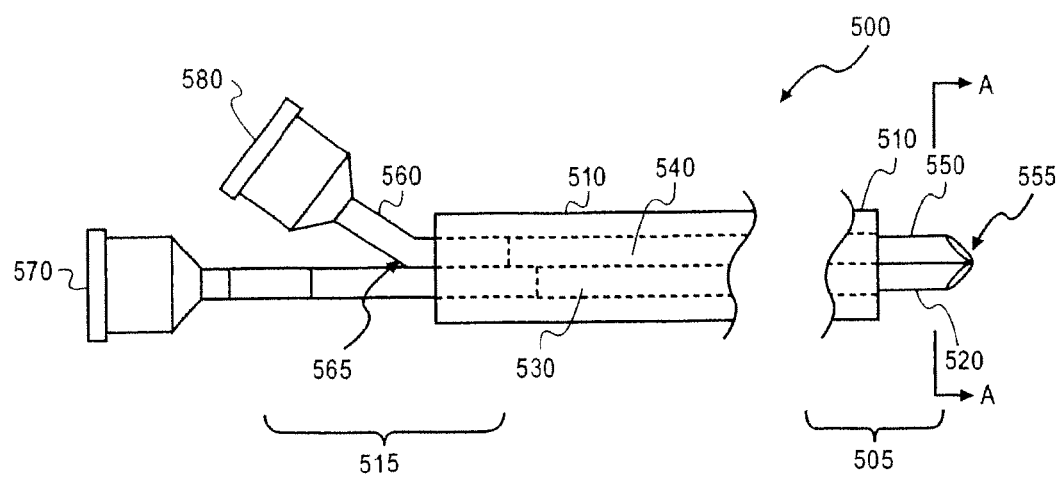
FIGS. 5A-5B illustrate an alternative embodiment of a dual bore delivery device.
Figure 5B:
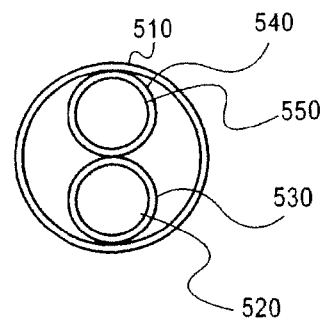

FIGS. 5A-5B illustrate an embodiment of a dual-needle injection device which can be used to deliver the compositions of the present invention. Delivery assembly 500 includes lumen 510 which may house delivery lumens, guidewire lumens and/or other lumens. Lumen 510, in this example, extends between distal portion 505 and proximal end 515 of delivery assembly 500.

In one embodiment, delivery assembly 500 includes first needle 520 movably disposed within delivery lumen 530. Delivery lumen 530 is, for example, a polymer tubing of a suitable material (e.g., polyamides, polyolefins, polyurethanes, etc.). First needle 520 is, for example, a stainless steel hypotube that extends a length of the delivery assembly. First needle 520 includes a lumen with an inside diameter of, for example, 0.08 inches (0.20 centimeters). In one example for a retractable needle catheter, first needle 520 has a needle length on the order of about 40 inches (about 1.6 meters) from distal portion 505 to proximal portion 515. Lumen 510 also includes auxiliary lumen 540 extending, in this example, co-linearly along the length of the catheter (from a distal portion 505 to proximal portion 515). Auxiliary lumen 540 is, for example, a polymer tubing of a suitable material (e.g., polyamides, polyolefins, polyurethanes, etc.). At distal portion 505, auxiliary lumen 540 is terminated at a delivery end of second needle 550 and co-linearly aligned with a delivery end of needle 520. Auxiliary lumen 540 may be terminated to a delivery end of second needle 550 with a radiation-curable adhesive, such as an ultraviolet curable adhesive. Second needle 550 is, for example, a stainless steel hypotube that is joined co-linearly to the end of main needle 520 by, for example, solder (illustrated as joint 555). Second needle 550 has a length on the order of about 0.08 inches (0.20 centimeters). FIG. 5B shows a cross-sectional front view through line A-A' of delivery assembly 500. FIG. 5B shows main needle 520 and second needle 550 in a co-linear alignment.

Referring to FIG. 5A, at proximal portion 515, auxiliary lumen 540 is terminated to auxiliary side arm 460. Auxiliary side arm 560 includes a portion extending co-linearly with main needle 520. Auxiliary side arm 560 is, for example, a stainless steel hypotube material that may be soldered to main needle 520 (illustrated as joint 565). Auxiliary side arm 560 has a co-linear length on the order of about, in one example, 1.2 inches (3 centimeters).

The proximal end of main needle 520 includes adaptor 570 for accommodating a substance delivery device (e.g., a component of a two-component bioerodable gel material). Adaptor 570 is, for example, a molded female luer housing. Similarly, a proximal end of auxiliary side arm 560 includes adaptor 580 to accommodate a substance delivery device (e.g., a female luer housing).

The design configuration described above with respect to FIGS. 5A-5B is suitable for introducing two-component gel compositions of the present invention. For example, a gel may be formed by a combination (mixing, contact, etc.) of a first component and a second component. Representatively, a first component may be introduced by a one cubic centimeter syringe at adaptor 570 through main needle 520. At the same time or shortly before or after, second component including a silk protein and optionally a least one cell type may be introduced with a one cubic centimeter syringe at adaptor 580. When the first and second components combine at the exit of delivery assembly 500 (at an infarct region), the materials combine (mix, contact) to form a bioerodable gel.

Figure 6A:
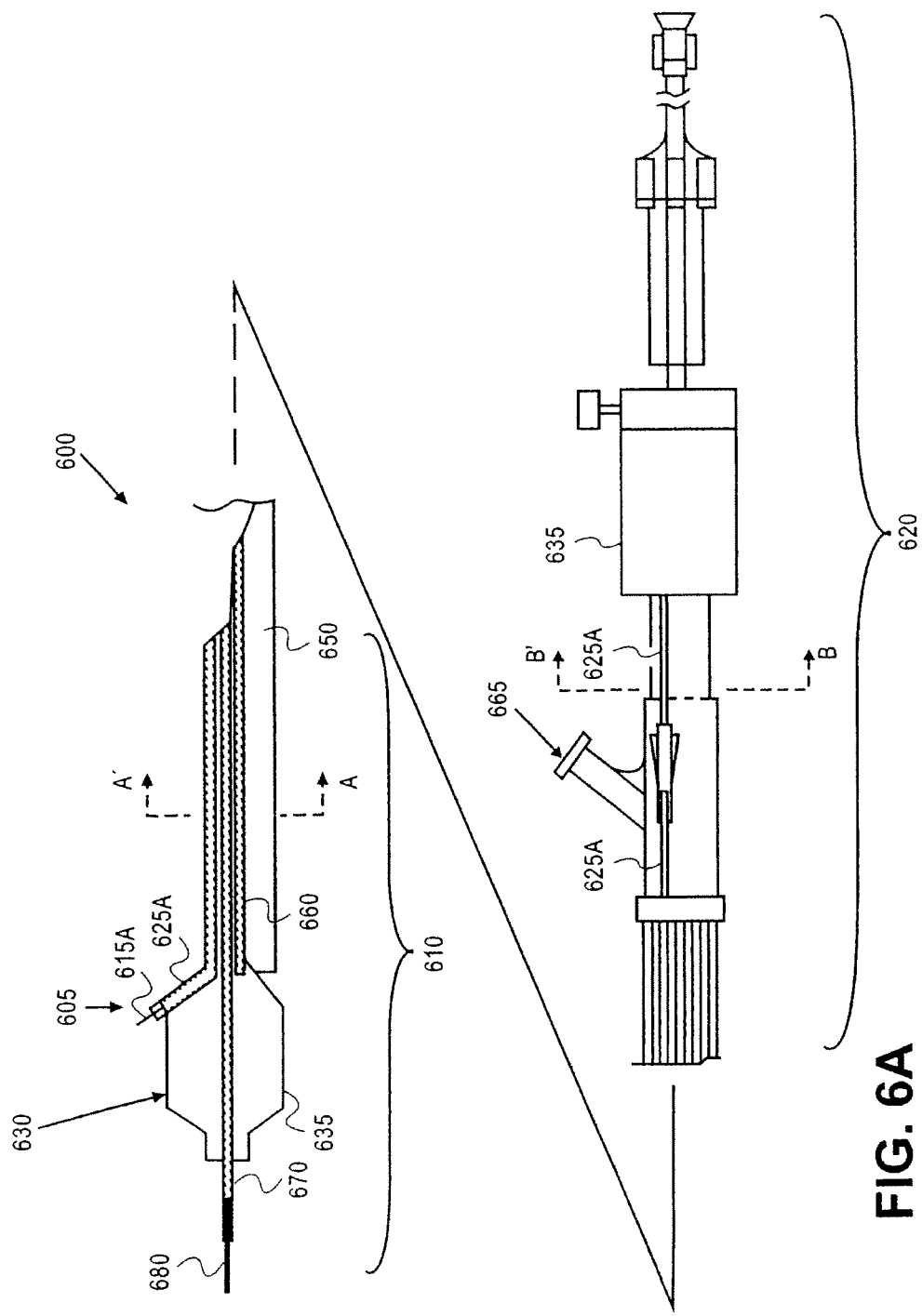
FIGS. 6A-6C illustrate a second alternative embodiment of a dual bore delivery device.
Figure 6B:
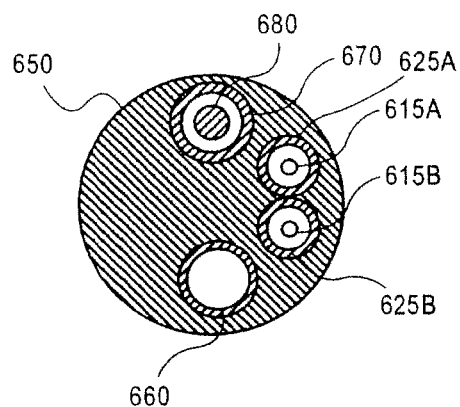
Figure 6C:
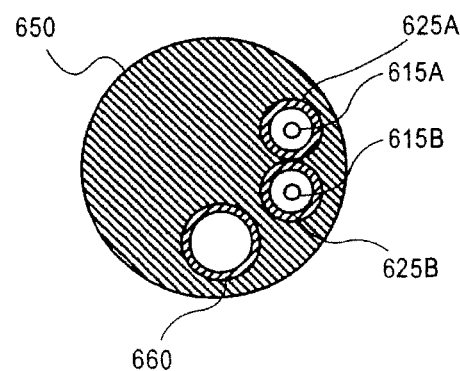

FIGS. 6A-6C illustrate an alternative embodiment of a dual-needle injection device which can be used to deliver two-component gel compositions of the present invention. In general, the catheter assembly 600 provides a system for delivering substances, such as two-component gel compositions, to or through a desired area of a blood vessel (a physiological lumen) or tissue in order to treat a myocardial infarct region. The catheter assembly 600 is similar to the catheter assembly 600 described in commonly-owned, U.S. Pat. No. 6,554,801, titled "Directional Needle Injection Drug Delivery Device", which is incorporated herein by reference.

In one embodiment, catheter assembly 600 is defined by elongated catheter body 650 having proximal portion 620 and distal portion 610. Guidewire cannula 670 is formed within catheter body (from proximal portion 610 to distal portion 620) for allowing catheter assembly 600 to be fed and maneuvered over guidewire 680. Balloon 630 is incorporated at distal portion 610 of catheter assembly 600 and is in fluid communication with inflation cannula 660 of catheter assembly 600.

Balloon 630 can be formed from balloon wall or membrane 635 which is selectively inflatable to dilate from a collapsed configuration to a desired and controlled expanded configuration. Balloon 630 can be selectively dilated (inflated) by supplying a fluid into inflation cannula 660 at a predetermined rate of pressure through inflation port 665 (located at proximal end 620). Balloon wall 635 is selectively deflatable, after inflation, to return to the collapsed configuration or a deflated profile. Balloon 630 may be dilated (inflated) by the introduction of a liquid into inflation cannula 660. Liquids containing treatment and/or diagnostic agents may also be used to inflate balloon 630. In one embodiment, balloon 630 may be made of a material that is permeable to such treatment and/or diagnostic liquids. To inflate balloon 630, the fluid can be supplied into inflation cannula 660 at a predetermined pressure, for example, between about one and 20 atmospheres. The specific pressure depends on various factors, such as the thickness of balloon wall 635, the material from which balloon wall 635 is made, the type of substance employed and the flow-rate that is desired.

Catheter assembly 600 also includes at least two substance delivery assemblies 605a and 605b (not shown; see FIGS. 6B-6C) for injecting a substance into a myocardial infarct region. In one embodiment, substance delivery assembly 605a includes needle 615a movably disposed within hollow delivery lumen 625a. Delivery assembly 605b includes needle 615b movably disposed within hollow delivery lumen 625b (not shown; see FIGS. 6B-6C). Delivery lumen 625a and delivery lumen 625b each extend between distal portion 610 and proximal portion 620. Delivery lumen 625a and delivery lumen 625b can be made from any suitable material, such as polymers and copolymers of polyamides, polyolefins, polyurethanes and the like. Access to the proximal end of delivery lumen 625a or delivery lumen 625b for insertion of needle 615a or 615b, respectively is provided through hub 635 (located at proximal end 620). Delivery lumens 625a and 625b may be used to deliver first and second components of a two-component gel composition to a post-myocardial infarct region.

FIG. 6B shows a cross-section of catheter assembly 600 through line A-A' of FIG. 6A (at distal portion 610). FIG. 6C shows a cross-section of catheter assembly 600 through line B-B' of FIG. 6A. In some embodiments, delivery assemblies 605a and 605b are adjacent to each other. The proximity of delivery assemblies 605a and 605b allows each component of the two-component gelation system to rapidly gel when delivered to a treatment site, such as a post-myocardial infarct region.

From the foregoing detailed description, it will be evident that there are a number of changes, adaptations and modifications of the present invention which come within the province of those skilled in the part. The scope of the invention includes any combination of the elements from the different species and embodiments disclosed herein, as well as subassemblies, assemblies and methods thereof. However, it is intended that all such variations not departing from the spirit of the invention be considered as within the scope thereof.

What is claimed is:

1. A method of treating a myocardial infarct in a subject comprising:
   simultaneously injecting from a dual bore delivery device into the myocardial infarct region of the subject (a) a first mixture comprising a first functionalized polyethylene glycol polymer and an extracellular matrix protein having at least one cell-adhesion site in a first buffer at physiological osmolality and (b) a second buffer at physiological osmolality to a post-myocardial infarct region, such that when the first mixture and the second buffer combine at the post-myocardial infarct region, a bioscaffolding is produced,
   wherein the extracellular matrix protein is selected from the group consisting of gelatin, laminin, elastin, and an arginine-glycine-aspartic acid peptide sequence.

2. The method of claim 1, further comprising a second functionalized polymer, wherein the second functionalized polymer is combined with one of the first mixture or the second buffer.

3. The method of claim 1, wherein the first functionalized polymer is one of an activated ester-terminated polyethylene glycol or a vinyl-terminated polyethylene glycol.

4. The method of claim 2, wherein the second functionalized polymer is one of a thiol-terminated polyethylene glycol or an amino-terminated polyethylene glycol.

5. The method of claim 2, wherein the first mixture has a pH of less than 6.5.

6. The method of claim 1, wherein the second buffer has a pH in a range from 7.5 to 9.0.

7. The method of claim 1, wherein the physiological osmolality is in a range from 280 mOsm/kg $H_2O$ to 300 mOsm/kg $H_2O$.

8. The method of claim 1, wherein the second buffer has a concentration in the range of 140 mM to 150 mM.

9. The method of claim 1, wherein the first mixture further comprises one of a cell, a growth factor or a combination thereof.

10. The method of claim 9, wherein the cell, the growth factor, or the combination thereof is combined with the first mixture.

11. The method of claim 9, wherein the growth factor is selected from the group consisting of vasoendothelial growth factor (VEGF), fibroblast growth factor (FGF), Del 1, hypoxia inducing factor (HIF), monocyte chemoattractant protein (MCP), nicotine, platelet derived growth factor (PDGF), insulin-like growth factor 1 (IGF-1), transforming growth factor (TGF), hepatocyte growth factor (HGF), estrogens, follistatin, proliferin, prostaglandin E1 (PGE1) and E2 (PGE2), tumor necrosis factor (TNF), Interleukin 8 (IL-8), hematopoietic growth factors, erythropoietin (EPO), granulocyte-colony stimulating factors (G-CSF) and platelet-derived endothelial growth factor (PD-ECGF).

12. The method of claim 9, wherein the cell is selected from the group consisting of localized cardiac progenitor cells, mesenchymal stem cells, bone marrow derived mononuclear cells, adipose tissue derived stem cells, embryonic siem cells, umbilical-cord-blood-derived stem cells, smooth muscle cells and skeletal myoblasts.

13. The method of claim 2, wherein the first functionalized polymer and the second functionalized polymer collectively have a functionality greater than four.

14. The method of claim 2, wherein the first mixture and the second buffer comprise a gel at pH 7.2 when combined.

* * * * *

SEQUENCE LISTING

<160> NUMBER OF SEQ ID NOS: 3

<210> SEQ ID NO 1
<211> LENGTH: 16
<212> TYPE: PRT
<213> ORGANISM: Unknown
<220> FEATURE:
<223> OTHER INFORMATION: Self-assembled peptide

<400> SEQUENCE: 1

Arg Ala Arg Ala Asp Ala Asp Ala Arg Ala Arg Ala Asp Ala Asp Ala

```
<210> SEQ ID NO 2
<211> LENGTH: 20
<212> TYPE: PRT
<213> ORGANISM: Unknown
<220> FEATURE:
<223> OTHER INFORMATION: Self-assembled peptide

<400> SEQUENCE: 2

Val Lys Val Lys Val Lys Val Lys Val Pro Pro Thr Lys Val Lys Val
1               5                   10                  15

Lys Val Lys Val
            20

<210> SEQ ID NO 3
<211> LENGTH: 16
<212> TYPE: PRT
<213> ORGANISM: Unknown
<220> FEATURE:
<223> OTHER INFORMATION: Self-assembled peptide

<400> SEQUENCE: 3

Ala Glu Ala Glu Ala Lys Ala Lys Ala Glu Ala Glu Ala Lys Ala Lys
1               5                   10                  15
```